(12) United States Patent
Gordon et al.

(10) Patent No.: US 12,315,648 B2
(45) Date of Patent: *May 27, 2025

(54) RADIATION SHIELDING DEVICES, SYSTEMS, AND METHODS

(71) Applicant: Radux Devices, LLC, Omaha, NE (US)

(72) Inventors: Gregory Gordon, Omaha, NE (US); Andrew Ubel, St. Paul, MN (US)

(73) Assignee: Radux Devices, LLC, Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/595,895

(22) Filed: Mar. 5, 2024

(65) Prior Publication Data

US 2024/0290512 A1   Aug. 29, 2024

Related U.S. Application Data

(63) Continuation of application No. 18/100,844, filed on Jan. 24, 2023, now Pat. No. 11,948,701, which is a
(Continued)

(51) Int. Cl.
*G21F 3/00* (2006.01)
*A61B 6/10* (2006.01)
(Continued)

(52) U.S. Cl.
CPC ............... *G21F 3/00* (2013.01); *A61B 6/107* (2013.01); *G21F 1/085* (2013.01); *G21F 5/015* (2013.01);
(Continued)

(58) Field of Classification Search
CPC .. A61B 6/107; A61N 5/10; A61N 2005/1094; G21F 3/00
(Continued)

(56) References Cited

U.S. PATENT DOCUMENTS 2,497,749 A   2/1950   Wagner
2,794,128 A   5/1957   Shasky
(Continued)

FOREIGN PATENT DOCUMENTS

CA    2091608       9/1994
CN    101312691    11/2008
(Continued)

OTHER PUBLICATIONS

EP Extended Search Report in European Appln. No. 19796105.5, dated Jul. 23, 2021, 10 pages.
(Continued)

*Primary Examiner* — Nicole M Ippolito
(74) *Attorney, Agent, or Firm* — Fish & Richardson P.C.

(57) ABSTRACT

In general, radiation shielding systems that shield radiation from multiple directions are described. In one embodiment, a method of shielding radiation is provided, including supporting a shielding device on an object proximate a radiation source, positioning a first shielding portion in a vertical position relative to the object, positioning a second shielding portion to extend away from the first portion, the second shielding portion attached to the first portion, and shielding radiation from the radiation source by the first shielding portion and the second shielding portion such that the first and second shielding portions provide a radiation shielding zone for a healthcare practitioner.

20 Claims, 13 Drawing Sheets

Related U.S. Application Data continuation of application No. 17/569,829, filed on Jan. 6, 2022, now Pat. No. 11,587,692, which is a continuation of application No. 17/086,036, filed on Oct. 30, 2020, now Pat. No. 11,222,732, which is a continuation of application No. 16/707,732, filed on Dec. 9, 2019, now Pat. No. 10,861,611, which is a continuation of application No. 15/972,016, filed on May 4, 2018, now Pat. No. 10,517,550.

(51) Int. Cl.
*G21F 1/08* (2006.01)
*G21F 5/015* (2006.01)
*G21F 5/02* (2006.01)
*A61N 5/10* (2006.01)

(52) U.S. Cl.
CPC ........ *G21F 5/02* (2013.01); *A61N 2005/1094* (2013.01)

(58) Field of Classification Search
USPC ......... 250/505.1, 506.1, 515.1, 516.1, 517.1, 250/519.1
See application file for complete search history.

(56) References Cited

U.S. PATENT DOCUMENTS

| | | | |
|---|---|---|---|
| 3,016,255 A | 1/1962 | Russel | |
| 3,172,240 A | 3/1965 | Giardini et al. | |
| 3,239,669 A | 3/1966 | Weinberger | |
| 3,303,717 A | 2/1967 | Valenti | |
| 3,409,317 A | 11/1968 | James | |
| 3,883,749 A | 5/1975 | Whittaker et al. | |
| 4,220,867 A | 9/1980 | Bloch, Jr. | |
| 4,280,056 A | 7/1981 | Renshaw | |
| 4,581,538 A | 4/1986 | Lenhart | |
| 4,751,747 A | 6/1988 | Banks et al. | |
| D300,945 S | 5/1989 | Fleming et al. | |
| 4,872,714 A | 10/1989 | Brusasco | |
| 4,917,413 A | 4/1990 | Jason et al. | |
| 4,923,162 A | 5/1990 | Fleming et al. | |
| 4,938,233 A | 7/1990 | Orrison, Jr. | |
| 5,090,044 A | 2/1992 | Kobayahi | |
| 5,125,115 A | 6/1992 | Lincoln | |
| RE34,120 E | 11/1992 | Plahn | |
| 5,319,349 A | 6/1994 | Smith | |
| D349,577 S | 8/1994 | Sayles | |
| 5,398,176 A | 3/1995 | Ahuja | |
| 5,521,803 A | 5/1996 | Eckert | |
| 5,522,403 A | 6/1996 | Bark | |
| 5,523,581 A | 6/1996 | Cadwalader | |
| 5,569,090 A | 10/1996 | Hoskins et al. | |
| 5,628,062 A | 5/1997 | Tseng | |
| 5,638,545 A | 6/1997 | Rosner | |
| 5,704,662 A | 1/1998 | Kwiatkowski | |
| 5,711,027 A | 1/1998 | Katz et al. | |
| 5,949,020 A | 9/1999 | Mitchell et al. | |
| 5,981,964 A | 11/1999 | McAuley et al. | |
| 5,992,823 A | 11/1999 | Hung-Lin et al. | |
| 6,135,032 A | 10/2000 | Ko et al. | |
| 6,217,087 B1 | 4/2001 | Fuller et al. | |
| 6,325,538 B1 | 12/2001 | Heesch | |
| 6,394,724 B1 | 5/2002 | Kelly et al. | |
| 6,703,632 B1 | 3/2004 | Macklis | |
| 6,835,945 B2 | 12/2004 | Mossor | |
| 7,057,194 B2 | 6/2006 | Goldstein | |
| 7,099,427 B2 | 8/2006 | Cadwalader et al. | |
| 7,112,811 B2 | 9/2006 | Lemer | |
| 7,226,234 B2 | 6/2007 | Gordy et al. | |
| 7,521,615 B1 | 4/2009 | Ho et al. | |
| 7,638,784 B2 | 12/2009 | Fox et al. | |
| 7,663,128 B2 | 2/2010 | Arterson | |
| 8,015,714 B2 | 9/2011 | Dekort et al. | |
| 8,032,994 B2 | 10/2011 | Waddell et al. | |
| 8,334,524 B2 | 12/2012 | DeMeo et al. | |
| 8,445,093 B2 | 5/2013 | Lemer | |
| 8,664,628 B2 | 3/2014 | Yoder | |
| 8,716,687 B2 | 5/2014 | Goldstein | |
| 8,835,887 B2 | 9/2014 | Beck | |
| D716,449 S | 10/2014 | Ballsieper | |
| D772,415 S | 11/2016 | Ballsieper | |
| D775,340 S | 12/2016 | Ballsieper | |
| 9,697,920 B2 | 7/2017 | Gordon et al. | |
| 10,010,297 B2 | 7/2018 | Gordon | |
| 10,517,550 B2 * | 12/2019 | Gordon | G21F 5/02 |
| 10,861,611 B2 * | 12/2020 | Gordon | G21F 3/00 |
| 11,222,732 B2 * | 1/2022 | Gordon | G21F 3/00 |
| 11,587,692 B2 * | 2/2023 | Gordon | A61B 6/107 |
| 11,948,701 B2 * | 4/2024 | Gordon | G21F 3/00 |
| 2003/0132639 A1 | 7/2003 | Franklin | |
| 2003/0209387 A1 | 11/2003 | Burr | |
| 2004/0041107 A1 | 3/2004 | Cadwalader | |
| 2004/0169114 A1 | 9/2004 | Dierkes | |
| 2004/0183316 A1 | 9/2004 | Walls et al. | |
| 2005/0023842 A1 | 2/2005 | Johnson et al. | |
| 2005/0104435 A1 | 5/2005 | Bain et al. | |
| 2005/0213712 A1 | 9/2005 | Cadwalader et al. | |
| 2006/0251219 A1 | 11/2006 | Cadwalader et al. | |
| 2007/0029513 A1 | 2/2007 | Treuth | |
| 2008/0056813 A1 | 3/2008 | Viernekes | |
| 2008/0128297 A1 | 6/2008 | Rose | |
| 2008/0182093 A1 | 7/2008 | Sonntag et al. | |
| 2009/0045358 A1 | 2/2009 | Arterson | |
| 2010/0249709 A1 | 9/2010 | Fischvogt | |
| 2010/0289718 A1 | 11/2010 | Kang et al. | |
| 2010/0304060 A1 | 12/2010 | Lemer | |
| 2010/0324433 A1 | 12/2010 | Wilson et al. | |
| 2011/0248193 A1 | 10/2011 | Goldstein | |
| 2011/0288489 A1 | 11/2011 | Bierman et al. | |
| 2012/0051502 A1 | 3/2012 | Ohta | |
| 2012/0132217 A1 | 5/2012 | Rees | |
| 2012/0241652 A1 | 9/2012 | Jeschke | |
| 2012/0246790 A1 | 10/2012 | Salcedo | |
| 2012/0272483 A1 | 11/2012 | Moore | |
| 2012/0324614 A1 | 12/2012 | Steinberg et al. | |
| 2013/0266122 A1 | 10/2013 | Patil et al. | |
| 2013/0320246 A1 | 12/2013 | Beck | |
| 2014/0021377 A1 | 1/2014 | Khandkar et al. | |
| 2014/0029720 A1 | 1/2014 | Osherov et al. | |
| 2014/0048730 A1 | 2/2014 | Niedzielski et al. | |
| 2015/0041686 A1 | 2/2015 | Pizarro | |
| 2016/0027540 A1 | 1/2016 | Gordon | |
| 2016/0220199 A1 | 8/2016 | Gordon | |
| 2016/0317110 A1 | 11/2016 | Rees | |
| 2017/0119324 A1 | 5/2017 | Wilson et al. | |
| 2017/0309357 A1 | 10/2017 | Gordon et al. | |
| 2018/0289343 A1 | 10/2018 | Gordon | |

FOREIGN PATENT DOCUMENTS

| | | |
|---|---|---|
| CN | 102781334 | 11/2012 |
| CN | 107072611 | 8/2017 |
| DE | 2714859 | 10/1978 |
| DE | 3326880 | 2/1985 |
| DE | 29604146 | 4/1996 |
| DE | 20003841 | 5/2000 |
| DE | 202008002237 | 7/2009 |
| EP | 1484264 | 12/2004 |
| EP | 1526603 | 4/2005 |
| EP | 1541897 | 6/2005 |
| EP | 3046475 A1 | 7/2016 |
| FR | 2439460 | 5/1980 |
| GB | 2472246 | 2/2011 |
| JP | S39-009443 | 1/1964 |
| JP | S51-019380 | 2/1976 |
| JP | S52-112075 | 9/1977 |
| JP | H03-502182 | 5/1991 |
| JP | H05-038685 | 2/1993 |
| JP | H07-229999 | 8/1995 |
| JP | 2003-533245 | 11/2003 |
| JP | 2004-264207 | 9/2004 |
| JP | WO 2004/011824 | 11/2005 |

(56) References Cited

FOREIGN PATENT DOCUMENTS

| JP | 2007-212304 | 8/2007 |
|---|---|---|
| JP | 2010-521992 | 7/2010 |
| JP | 2010-525910 | 7/2010 |
| JP | 2011-516165 | 5/2011 |
| JP | 2013-015369 | 1/2013 |
| JP | 2013-512745 | 4/2013 |
| JP | 2015-206643 | 11/2015 |
| JP | 2017-524938 | 8/2017 |
| KR | 10-2009030459 | 3/2009 |
| WO | WO 1989/05216 | 6/1989 |
| WO | WO 2005/094272 | 10/2005 |
| WO | WO 2008/086338 | 7/2008 |
| WO | WO 2008/140486 | 11/2008 |
| WO | WO 2012/049469 | 4/2012 |
| WO | WO 2015/042419 | 3/2015 |
| WO | WO 2017/116530 | 11/2017 |

OTHER PUBLICATIONS

Extended European Search Report for European Application No. 14/845,264.2, dated Sep. 1, 2016, 11 pages.
Extended European Search Report in International Application No. EP14898038.6, dated Apr. 9, 2018, 8 pages.
Gordon et al, "Lock-block central venous occlusion intervention," Powerpoint, Presented at the Radiological Society of North America Conference, Nov. 27, 2016, 20 pages.
Gordon, "Radiation exposure during chronic central venous occlusion interventions: a stimulation study comparing two radiation protection devices," Poster, Presented at Proceedings of the Society of Interventional Radiology 2017 conference, Mar. 4, 2017, 1 page.
Health Physics Society, "Lead Garments (Aprons, Gloves, etc.)," hps.org [online], Aug. 13, 2014 [retrieved on Jan. 12, 2015]. Retrieved from the Internet: <URL:http://hps.org/publicinformation/ate/faqs/leadgarmentsfaq.html>, 8 pages.
International Preliminary Report on Patentability in International Application No. PCT/US2014/056565, Mailed Feb. 9, 2017, 10 pages.
International Preliminary Report on Patentability in International Application No. PCT/US2014/056585, dated Mar. 22, 2016, 5 pages.
International Search Report and Written Opinion in International Application No. PCT/US2014/056565, Mailed Aug. 23, 2015, 13 pages.
International Search Report and Written Opinion in International Application No. PCT/US2014/056585, dated Dec. 26, 2014, 8 pages.
International Search Report and Written Opinion in International Application No. PCT/US2019/028992, dated Jul. 29, 2019, 8 pages.
Japanese Office Action in Application No. JP2016-544024, dated Jun. 18, 2018, 9 pages (with Machine translation).
Japanese Office Action in Application No. JP2017-504074, mailed Jun. 4, 2018, 11 pages (with English Translation).
Mettler et al., "Radiologic and Nuclear Medicine Studies in the United States and Worldwide: Frequency, Radiation Dose, and Comparison with Other Radiation Sources—1950-2007," Radiology, Nov. 2009, 253(2): 520-531.
Naidu et al., "Radiation exposure to personnel performing endoscopic retrograde cholangiopancreatography," Postgrad Med J., 81(960):660-662, Oct. 2005.
Whitby and Martin, "Investigation using an advanced extremity gamma instrumentation system of options for shielding the hand during the preparation and injection of radiopharmaceuticals," J Radiol Prot., 23(1):79-96, Mar. 2003.

\* cited by examiner

RADIATION SHIELDING DEVICES, SYSTEMS, AND METHODS

CROSS-REFERENCE TO RELATED APPLICATIONS

This application is a continuation of and claims priority to U.S. application Ser. No. 18/100,844, filed on Jan. 24, 2023, which is a continuation of U.S. application Ser. No. 17/569,829 filed on Jan. 6, 2022 (now U.S. Pat. No. 11,587,692), which is a continuation of and claims priority to U.S. application Ser. No. 17/086,036, filed on Oct. 30, 2020 (now U.S. Pat. No. 11,222,732), which is a continuation of and claims priority to U.S. application Ser. No. 16/707,732, filed Dec. 9, 2019 (now U.S. Pat. No. 10,861,611), which is a continuation application of and claims priority to U.S. application Ser. No. 15/972,016, filed on May 4, 2018 (now U.S. Pat. No. 10,517,550). The disclosure of the prior applications are considered part of (and are incorporated by reference in) the disclosure of this application.

TECHNICAL FIELD

This document describes devices, systems and methods for shielding radiation, such as portable radiation shielding devices for use in shielding healthcare practitioners from radiation.

BACKGROUND

Healthcare practitioners often work near a radiation field, such as from a fluoroscope, X-ray machine, or other imaging system, when treating a patient. Procedures and therapies are often designed to reduce patient exposure while allowing healthcare practitioners to effectively treat the patient. However, cumulative radiation exposure of physicians and healthcare practitioners may be significant as they often perform multiple treatments in a typical day, and radiation exposure may be increased when a particular treatment requires the healthcare practitioner's body to be close to a field of radiation. For example, the healthcare practitioner's hands may be exposed to radiation from fluoroscopic imaging equipment when inserting a catheter in a patient's vessel, or when delivering other instruments, medicines, fluids, or other endovascular devices in a patient's vessel. Various techniques have been used to limit radiation exposure, such as physical barriers including radiation shielding and body wear.

SUMMARY

Some embodiments described herein include devices, systems, and methods that can be used to provide protection for a healthcare practitioner, such as a physician, nurse, technician, etc., during a medical procedure. For example, a radiation shielding device may shield direct and scatter radiation from multiple directions, such as by providing shielding in a generally horizontal orientation and in a generally vertical orientation.

In some optional embodiments, multiple types of shielding appliances may be connected to a single base (e.g., in user-selectable positions) to shield the healthcare practitioner while facilitating efficient workflow in an operating environment. The shielding appliances may include first and second appliances that differ in one or more characteristics, such as a relatively rigid and/or shape-stable radiation shield and a relatively flexible and/or non-shape-stable radiation shielding drape. The shield may extend at least partially in a first direction (e.g., a substantially vertical orientation) and the drape may extend at least partially in a second direction different from the first direction (e.g., at least partially in a substantially horizontal orientation orthogonal to the shield).

In other optional embodiments, the shielding appliance may include first and second portions, which may be different portions of a single unit or of a multi-appliance assembly. The portions may optionally differ in one or more characteristics, such as a relatively rigid and/or shape-stable radiation shielding first portion and a relatively flexible and/or non-shape-stable radiation shielding second portion. Alternatively, both portions can be similarly flexible and/or shape adjusting. The first portion may extend at least partially in a first direction (e.g. a substantially vertical orientation) and the second portion may extend at least partially in a second direction different from the first direction (e.g. at least partially in a substantially horizontal orientation orthogonal to the shield). The shielding device can protect the healthcare practitioner's hands, arms, and body that may otherwise be exposed to relatively higher levels of radiation. In various example configurations, each of the first and second shielding appliances (or portions) are fabricated from a radiation shielding material such that unsafe levels on first sides of the first and/or second shielding appliances (or portions) may be reduced to safe levels on second sides of the first and/or second shielding appliances (or portions).

In some example embodiments, a base may be supported partially or entirely on a patient in close proximity to a radiation source and/or an imaging location. In some optional embodiments, the radiation shield (or first portion of a device) may be manipulated by a user to a selected orientation relative to the base (or to the second portion) during set-up in the operating environment, and optionally locked into the selected orientation. Alternatively, or additionally, the radiation drape (or second portion of device) may be arranged to provide a selected coverage area by unfolding or unrolling the drape (e.g., while the drape is attached to a base).

Particular embodiments described herein provide a method of shielding radiation, comprising: attaching an optional base to an object proximate a radiation source, positioning a first shielding appliance relative to the base, the first shielding appliance attached to the base and having a first side facing towards the radiation source, a second side facing away from the radiation source, a top edge positioned above the base and a bottom edge positioned above the base, positioning a second shielding appliance to extend away from the base, the second shielding appliance attached to the base, and shielding radiation from the radiation source by the first shielding appliance and the second shielding appliance such that the first and second shielding appliances provide a radiation shielding zone for a healthcare practitioner.

In some implementations, the system may optionally include one or more of the following features. The first shielding appliance may be a shape-stable shield. The second shielding appliance may be a non-shape-stable radiation shielding drape. The method may include attaching the first shielding appliance to the base after attaching the base to the object. The method may include attaching the second shielding appliance to the base after attaching the base to the object. The base may include a first adhesive layer configured to adhere to the object and a second adhesive layer on a surface of the base opposite the first adhesive layer, the second shielding appliance adhered to the base by the second adhesive layer. Alternatively, or additionally, the second shielding appliance may include a first adhesive layer configured to adhere to the object and a second adhesive layer on a surface opposite the first adhesive layer configured to adhere to the base. The second shielding appliance, in some optional embodiments, preferably does not substantially extend away from the base on the first side of the first shielding appliance so as to not block the radiation from reaching its intended object. The method may include positioning a tubular medical device to extend on both sides of the first shielding appliance (or first portion), the tubular medical device positioned below the first shielding appliance and above the second shielding appliance while the first and second shielding appliances are attached to the base. The base may be supported on a patient. The method may include adjusting the radiation source to a height lower than a height of the top edge of the first shielding appliance. The method may include separating the base from the first shielding appliance after performing a medical operation, disposing of at least a portion of the base and the second shielding appliance, and sterilizing the first shielding appliance. An angle defined between the first shielding appliance and the second shielding appliance proximate the base may be between about 75° and 105°.

In other implementations, the system may optionally include one or more of the following features. The first shielding portion of the device may be a shape-stable shield. The second shielding portion of the device may be a non-shape-stable radiation shielding drape. The method may include attaching the device to the object, e.g., using an adhesive layer affixed to the patient side of the second portion. The second portion may include a first adhesive layer configured to adhere to the object. The method may include positioning a tubular medical device to extend on both major faces of the first shielding portion, the tubular medical device positioned below the first shielding portion and above the second shielding portion while the first and second shielding portions are attached to the patient. The method may include adjusting the radiation source to a height lower than a height of the top edge of the first shielding portion. An angle defined between the first shielding portion and the second shielding portion may be between about 75° and 105°.

In one implementation the first and second portions of the system are formed from a single sheet of a radiation shielding material, wherein the first and second portions are folded in a manner to orient the first portion and the second portion in a roughly perpendicular fashion. I.e., the first portion is generally positioned vertically to the patient while the second portion is positioned roughly horizontally to the patient. The system preferably further comprises structure to maintain the first and second portions in the aforementioned configuration. For example, the shielding material can be constructed using a shape stable sheet of a foil that can support the system when configured as described herein. Alternatively, the system may comprise optional structural supports that are contained within or attached to the system to hold the first portion in the aforementioned configuration relative to the second portion and to the object. In some embodiments, suitable support structures may include bendable wires, bendable rods, bendable stiffened sheets, bendable tubes, gas or liquid inflatable channels, etc.

Particular embodiments described herein provide a method of shielding radiation, comprising adhering a radiation shielding device to an object proximate a radiation source, the radiation shielding device comprising an optional base including a first adhesive layer configured to adhere the radiation shielding device to the object, a shape-stable radiation shield attached to the optional base, the shape-stable radiation shield having a top edge, a bottom edge, a first major face oriented towards a radiation source, and a second major face opposite the first major face, and a non-shape-stable radiation shielding drape adhered to the base. The method may further include expanding the non-shape-stable radiation shielding drape to extend away from the optional base, and shielding radiation from the radiation source by the shape-stable radiation shield and the non-shape-stable radiation shielding drape.

In some implementations, the system may optionally include one or more of the following features. The method may include positioning the radiation source at least partially at a height between the top edge of the shape-stable radiation shield and the base (or between the top edge of the first portion and the junction between the first and second portions). The optional base may be positioned between the non-shape-stable radiation shielding drape and the object. The base may be positioned between the object and the shape-stable radiation shield. The method may include positioning a tubular medical device to extend on both sides of the shape-stable radiation shield, wherein the tubular medical device enters a patient at a location below the radiation source on a first side of the shape-stable radiation shield, and the non-shape-stable radiation shielding drape extends from the shape-stable radiation shield on a second side of the shape-stable radiation shield opposite the location below the radiation source, while radiation is emitted from the radiation source. The base may include a second adhesive layer located opposite the first adhesive layer, the second adhesive layer configured to adhere the non-shape-stable radiation shielding drape to the base.

Particular embodiments described herein provide a radiation shielding device, comprising a base including a first adhesive layer configured to adhere the base to an object, a first shielding appliance attached to the base, the first shielding appliance having a top edge, a bottom edge, a first major face configured to be oriented towards a radiation source, and a second major face opposite the first major face, and a second shielding appliance adhered to the base.

In some implementations, the system may optionally include one or more of the following features. The first shielding appliance may be a shape-stable shield and the second shielding appliance is a non-shape stable radiation shielding drape. The base may include a second adhesive layer on a surface of the base opposite the first adhesive layer, the second shielding appliance adhered to the base by the second adhesive layer. The second shielding appliance may extend away from the base on a first side of the first shielding appliance (e.g., opposite a target radiation area), and does not substantially extend away from the base on a second side of the first shielding appliance opposite the first side of the first shielding appliance (e.g., facing a target radiation area).

Particular embodiments described herein provide a method of assembling a radiation shield, comprising coupling a shape-stable shield to a base, coupling a non-shape-stable radiation shielding drape to the base, the non-shape-stable radiation shielding drape having a first contoured edge aligned with a portion of the base below a bottom edge of the shape-stable shield, the non-shape-stable radiation shielding drape expandable to extend from the base.

In some implementations, the system may optionally include one or more of the following features. The non-shape-stable radiation shielding drape (or second portion of a device) may be expandable to have a surface area that is at least twice a surface area of the shape-stable shield (or first portion of an appliance).

Particular embodiments described herein provide a radiation shielding device including a malleable radiation shielding appliance, and an opening defined through the radiation shielding appliance, the opening configured to allow passage of an interventional tool from a first side of the radiation shielding appliance to a second side of the radiation shielding appliance. The malleable radiation shielding appliance is configured to be manipulated into a user-selected configuration in which a first portion is oriented substantially vertically a second portion is oriented substantially horizontally relative to the first portion. shape-stable first radiation shielding portion. In some implementations, the first portion and the second portion may be integrally joined.

Particular embodiments described herein provide a method of shielding radiation, including supporting a shielding device on an object proximate a radiation source, the shielding device comprising a first shielding portion and a second shielding portion, positioning the first shielding portion in a vertical position relative to the object, wherein the first portion has a first side facing towards the radiation source, a second side facing away from the radiation source, and a top edge positioned above the second portion, positioning a second shielding portion to extend away from the first portion, the second shielding portion attached to the first portion, and shielding radiation from the radiation source by the first shielding portion and the second shielding portion such that the first and second shielding portions provide a radiation shielding zone for a healthcare practitioner.

In some implementations, the system may optionally include one or more of the following features. The method may include attaching the shielding device to the object. The first and second shielding portions may be integrally joined. The shielding device may include a malleable radiation shielding appliance, and the first shielding portion and the second shielding portion may be defined by the malleable radiation shielding appliance. An opening may be defined through an entire thickness of the shielding device, the opening configured to allow passage of an interventional tool from a first side of the first shielding portion to a second side of the first shielding portion. Positioning the first shielding portion and positioning the second shielding portion may include adjusting first and second fold locations. The first and second fold locations may be located between the first shielding portion and the second shielding portion. The object may be a patient subjected to radiation. The shielding device may include a first shielding appliance, the first shielding appliance may include the first shielding portion. The shielding device may include a second shielding appliance, the second shielding appliance may include the second shielding portion. The method may include attaching the first shielding appliance to the base and attaching the second shielding appliance to the base, a bottom edge of the first shielding appliance positioned above the base. The first shielding appliance may be a shape-stable shield and the second shielding appliance may be a non-shape-stable radiation shielding drape. The method may include attaching the second shielding appliance to the base after attaching the base to the object. The base may include a first adhesive layer configured to adhere to the object and a second adhesive layer on a surface of the base opposite the first adhesive layer. The method may include adjusting the radiation source to a height lower than a height of the top edge of the first shielding appliance. An angle defined between the first shielding portion and the second shielding portion is between about 75° and 105°.

Particular embodiments described herein provide a radiation shielding device, comprising a first shielding portion, a second shielding portion, and a folded region between the first and second shielding portions, the folded region defining an opening extending through a thickness of the radiation shielding device.

In some implementations, the system may optionally include one or more of the following features. The folded region may be manipulable to define an angle between about 0° and 195° (e.g., between about 165° and 195°) between the first shielding portion and the second shielding portion when in a first configuration, and an angle between about 75° and 105° between the first shielding portion and the second shielding portion when in a second configuration.

Particular embodiments described herein provide a radiation shielding device, comprising a base including a first adhesive layer configured to adhere the base to an object, a first shielding appliance attached to the base, the first shielding appliance having a top edge, a bottom edge, a first major face configured to be oriented towards a radiation source, and a second major face opposite the first major face, and a second shielding appliance adhered to the base. The first shielding appliance may be a shape-stable shield and the second shielding appliance is a non-shape stable radiation shielding drape.

Some embodiments of the devices, systems and techniques described herein may provide one or more of the following advantages. First, some embodiments described herein may reduce the level of radiation a healthcare practitioner may be exposed to. For example, an example radiation shielding device includes shielding appliances extending in multiple directions from the base (e.g., generally vertical and horizontal directions). Moreover, the radiation shielding device may provide a high level of protection from both direct radiation and scatter radiation directed towards the healthcare practitioner from a range of directions.

Second, some embodiments described herein may facilitate precise positioning of a first shielding appliance (e.g., shape-stable radiation shield) and/or second shielding appliance (e.g., non-shape stable radiation shielding drape) proximate a target area of radiation delivery. For example, in some optional embodiments, the optional base may provide an alignment aid that facilitates positioning of the second shielding appliance after the base and/or first shielding appliance has been attached to a patient or other support structure. Alternatively, or additionally, interference of the first and/or second shielding appliances with the radiation target area may be reduced, and the radiation dosage level emitted by the imaging system required to perform the operation may likewise be reduced.

Third, some embodiments described herein provide a high degree of radiation shielding while facilitating efficient operation by the healthcare practitioner. The radiation shielding device may be positioned in a user-selected location and/or a user-selected orientation. The flexibility in positioning and orienting the radiation shielding device allows the healthcare practitioner to position the device relative to the healthcare practitioner's preferred operating position. In some embodiments, the radiation shielding device may be partially or entirely malleable such that the healthcare practitioner may bend the radiation shielding device into a selected configuration, and the radiation shielding device will retain the selected configuration during operation. Alternatively, or additionally, the orientation of one or more shielding appliances may further enhance efficient operation by the healthcare practitioner, such as by providing a relatively larger area of protection that facilitates free movement by the healthcare practitioner during a medical procedure while the healthcare practitioner remains in an area substantially shielded from radiation exposure.

Fourth, some embodiments described herein provide an expandable shielding appliance having a coverage area that can be varied by the healthcare practitioner at the medical location. For example, the second radiation appliance may be foldable or rollable about itself such that a coverage area may be selectively increased or decreased by folding/rolling or unfolding/unrolling the second radiation appliance. In some embodiments, the second radiation appliance may be attached to the base in a folded or rolled condition, and selectively expanded by the healthcare practitioner when positioned in the operating environment (e.g., after the base is attached).

Fifth, some embodiments described herein facilitate efficient set-up of the medical location. For example, a radiation shielding device including multiple shielding appliances pre-attached or readily attachable to a common base may reduce the set-up required to shield the healthcare practitioner.

Sixth, some embodiments described herein facilitate efficient operation in the medical location. For example, a radiation shielding device including a notch or passage between the base and first shielding appliance may facilitate passage of a medical device (e.g., a tubular medical device, sheath, interventional tool, or other device) from a first side of the radiation shielding device (e.g., facing the healthcare practitioner) to a second side of the radiation shielding device (e.g., in the direct field of radiation below a radiation source). The healthcare practitioner may efficiently and effectively manipulate the device while the device has a direct path to a patient access point or other location within the direct field of radiation.

Seventh, some embodiments described herein facilitate flexible positioning of the radiation shielding device such that the healthcare practitioner can operate from a medically advantageous location of the patient. An operator may thus operate from a location selected primarily based on advantages in patient care while being less constrained by ergonomic or radiation dosage requirements, for example.

Eighth, some embodiments described herein provide a substantially continuous zone of protection by overlapping portions that are positioned at an angle relative to one another. For example, some example radiation shielding devices may include a substantially horizontal shielding portion and a substantially vertical portion. The radiation shielding device preferably does not include an unshielded break or opening between the substantially horizontal shielding portion and substantially vertical portion that allows a direct path for radiation to pass between first and second sides of the radiation shielding device, and thereby can provide a substantially continuous zone of protection for the healthcare practitioner.

The details of one or more implementations are set forth in the accompanying drawings and the description below. Other features and advantages will be apparent from the description and drawings, and from the claims.

DESCRIPTION OF DRAWINGS

The present description is further provided with reference to the appended Figures, wherein like structure is referred to by like numerals throughout the several views, and wherein.

DETAILED DESCRIPTION OF ILLUSTRATIVE EMBODIMENTS

Figure 1:
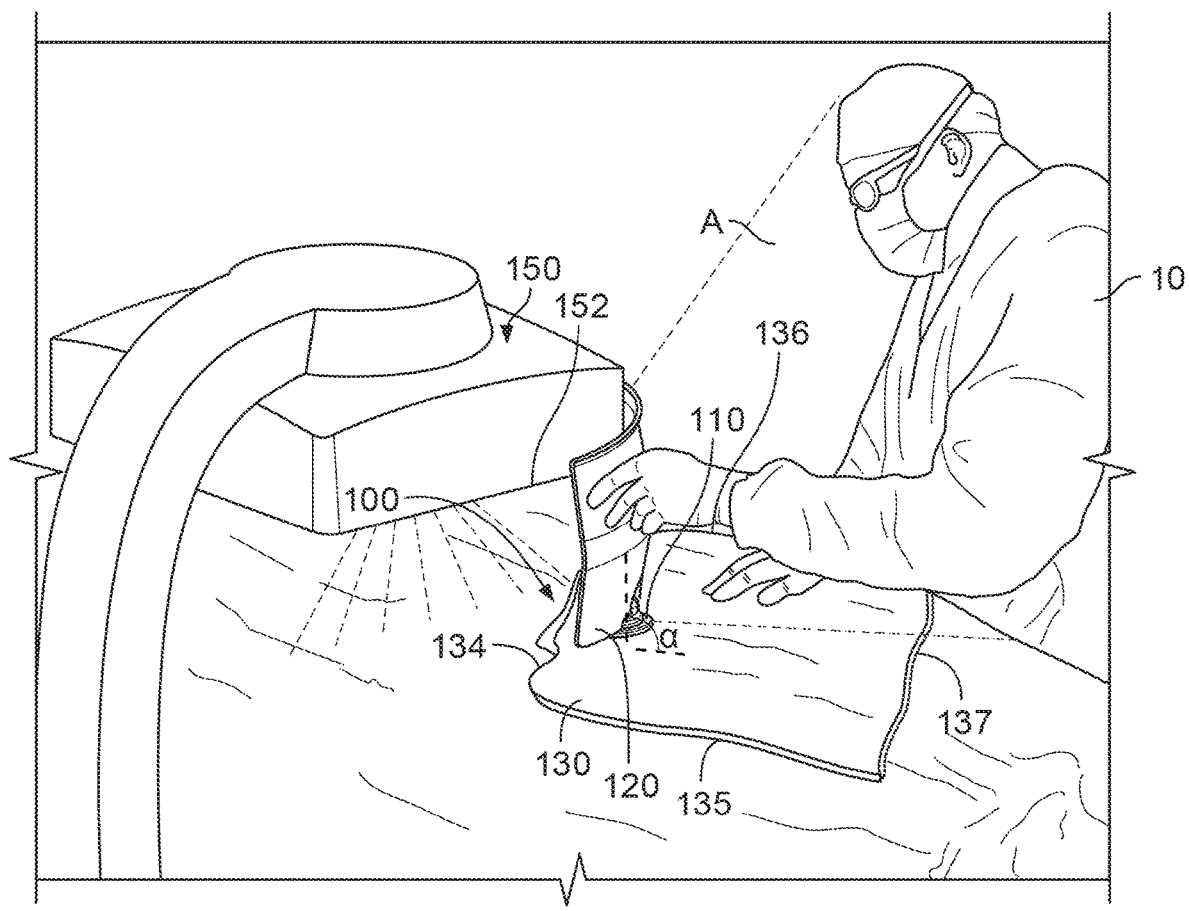
FIG. 1 is a perspective view of an example radiation shielding device in use in a medical environment, including first and second shielding appliances attached to a base.
Figure 2:
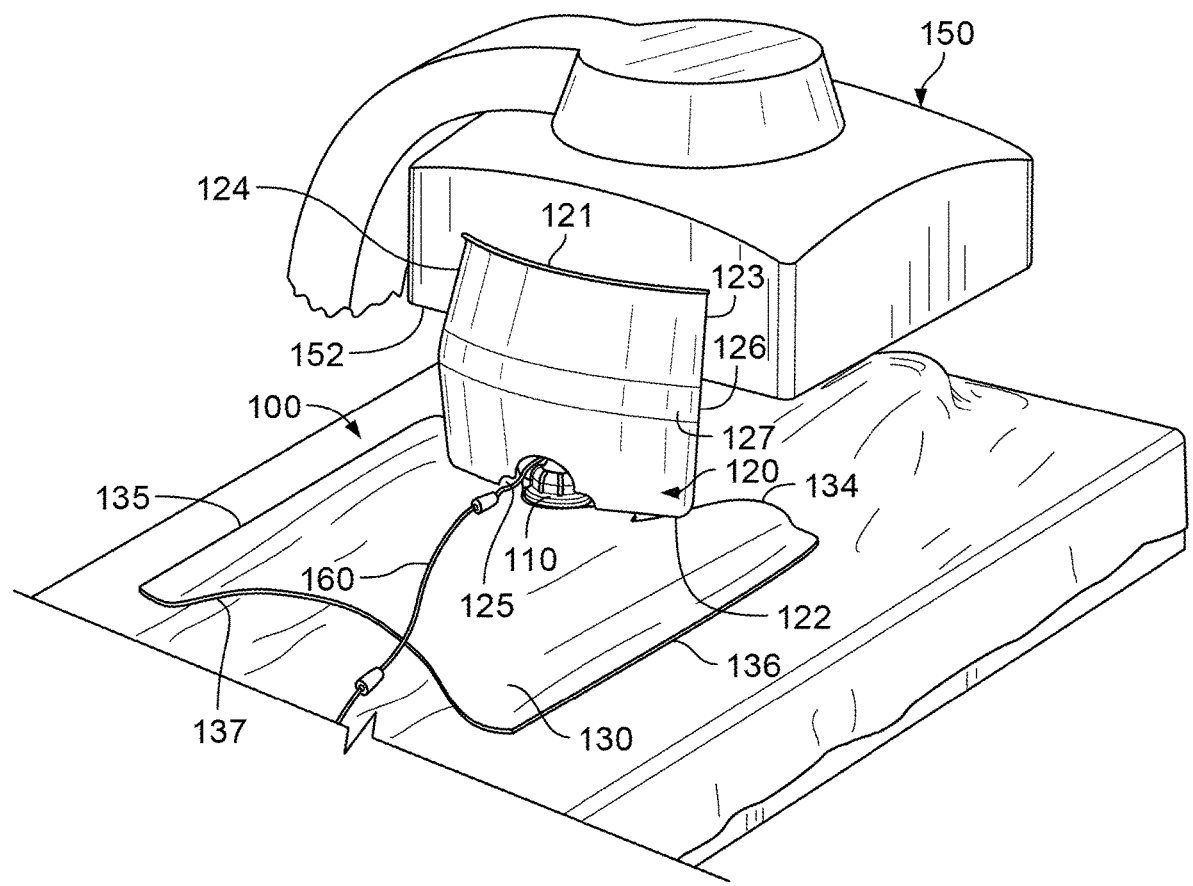
FIG. 2 is a perspective view of the example radiation shielding device of FIG. 1.
Figure 3:
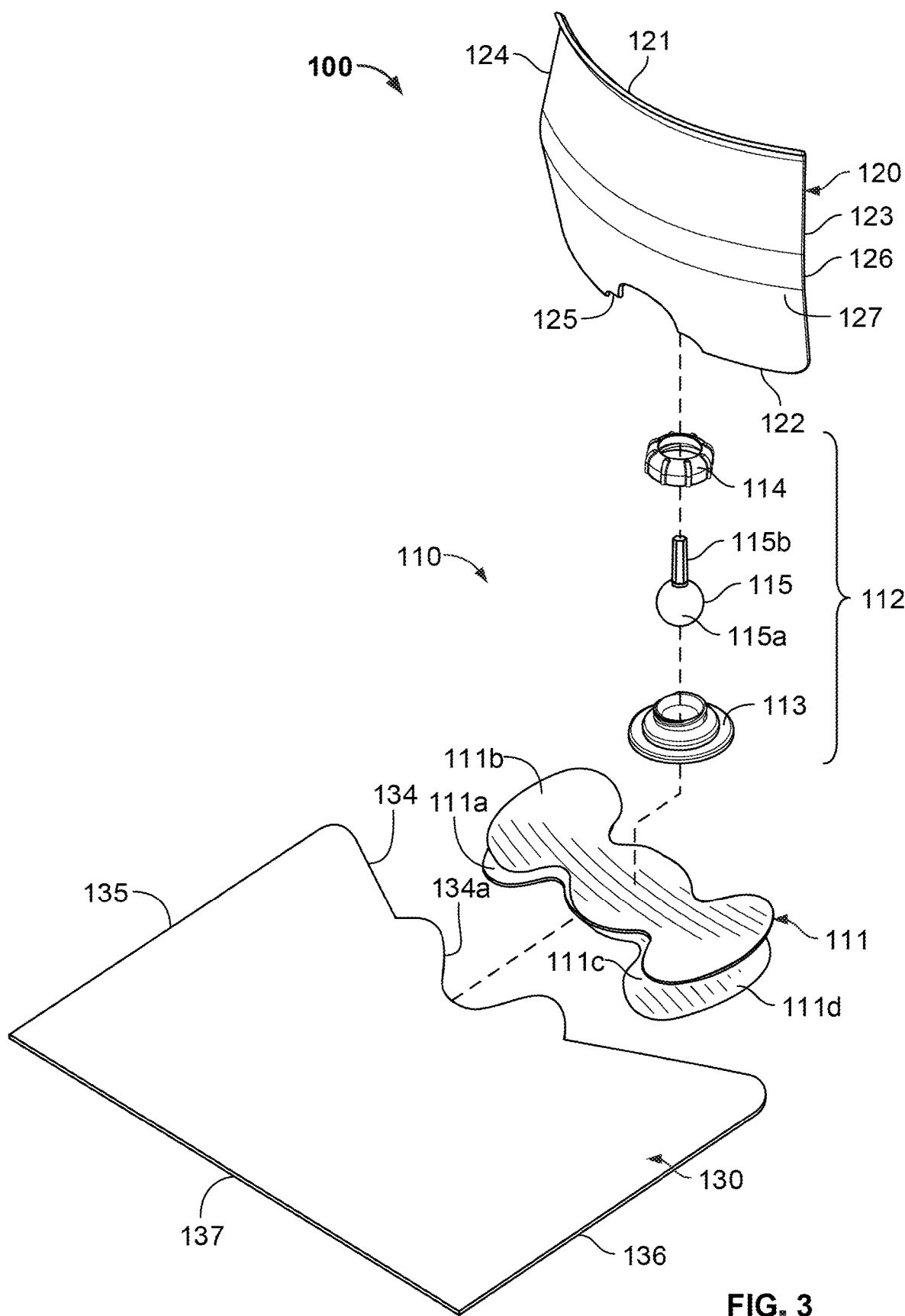
FIG. 3 is an exploded view of the example radiation shielding device of FIG. 1.

Referring to FIGS. 1-3, an example radiation shielding device 100 is shown, including a base 110, a first shielding appliance 120, and a second shielding appliance 130. The radiation shielding device 100 is positioned at least partially between a radiation source 150 (e.g., such as a medical imaging device) and a healthcare practitioner 10 to shield the healthcare practitioner 10 from radiation emitted by radiation source 150 during a medical operation. In some example embodiments, radiation shielding device 100 provides a radiation shielding zone A in which radiation exposure from radiation source 150 is eliminated or substantially reduced for the healthcare practitioner 10 operating within zone A. The first and second shielding appliances 120, 130 may be angled relative to one another such that radiation shielding device 100 provides a relatively large radiation shielding zone A while being relatively small, lightweight, and/or supportable on a patient.

Example radiation shielding device 100 may be supportable at least partially by a patient undergoing a medical operation. For example, the radiation shielding device 100 may be sufficiently compact and lightweight such that the device 100 may be entirely supported on a patient (e.g., without an additional base supported by the floor, ceiling, imaging device, or other structure in the medical environment). Such a configuration may facilitate efficient workflow by the healthcare practitioner 10, and facilitate positioning of radiation shielding device 100 proximate both radiation source 150 and a target location (e.g., a location being imaged and/or the target of radiation emitted by radiation source 150). Positioning of the radiation shielding device 100 close to the radiation source 150 and/or the target location facilitates a relatively large radiation protection zone A while shielding appliances 120 and 130 may be relatively small.

In some example embodiments, base 110 provides an attachment location for first and second shielding appliances 120, 130, and maintains first and second shielding appliances 120, 130 in a fixed location relative to base 110, radiation source 150, and/or the target location of the patient (e.g., during a medical operation). Base 110 provides sufficient mechanical strength and stiffness to support first and second shielding appliances 120, 130 during a medical operation, and/or while first and second shielding appliances 120, 130 are manipulated into a desired position, such as during a set-up procedure.

Healthcare practitioner 10 may arrange base 110, first shielding appliance 120, and second shielding appliance 130 prior to an operation involving radiation source 150. Base 110 may be supported, for example, on an object, such as the patient to be subjected to radiation emitted by radiation source 150. In some example embodiments, base 110, first shielding appliance 120, and/or second shielding appliance 130 are initially unconnected. Base 110 may be adhered to the object, such as surgical draping, the patient's skin, table, bed rail, or another object capable of supporting radiation shielding device 100, etc. by healthcare practitioner 10. Healthcare practitioner 10 may subsequently attach the first and second shielding appliances 120, 130 to base 110 to maintain the first and second shielding appliances 120, 130 in a fixed position relative to base 110, radiation source 150, and/or the patient. In some embodiments, first shielding appliance 120 and/or second shielding appliance 130 may be attached to base 110 before base 110 is attached to the object (e.g., assembled by healthcare practitioner 10 or assembled at a manufacturing location remote from the operating environment). Alternatively or additionally, first and/or second shielding appliances 120, 130 (e.g., such as a radiation shielding drape) may be positioned relative to a patient, and the base 110 subsequently attached (e.g., to second shielding appliance 130).

First and second shielding appliances 120, 130 may be independently positioned by healthcare practitioner 10 relative to base 110, radiation source 150, and/or the patient. Second shielding appliance 130 may be positioned at an angle relative to first shielding appliance 120. For example, radiation shielding device 100 defines an angle ($\alpha$) between surfaces of first shielding appliance 120 and second shielding appliance 130 (e.g., a second surface 127 of first shielding appliance 120 and a top surface of second shielding appliance 130). Angle ($\alpha$) may be selected by healthcare practitioner 10 considering, for example, the medical procedure being performed, the medical tools being used, the location of the procedure, the anatomy of the patient, etc. In various example embodiments, the angle ($\alpha$) defined between the first and second shielding appliances 120, 130, may be between about 135° and 45°, 105° and 75°, or about 90°. For example, first shielding appliance 120 may be oriented substantially vertically (e.g., vertically or otherwise within 15° of the direction of the gravitational force) and second shielding appliance 130 may be oriented substantially horizontally (e.g., horizontally or otherwise within 15° of perpendicular to the gravitational force). In some embodiments, the angle ($\alpha$) is an overall relative orientation of the first and second shielding appliances 120, 130, while the first and/or second shielding appliances may have non-planar portions or discrete surfaces of varying relative orientations.

In an example embodiment, at least first shielding appliance 120 is articulable relative to base 110 and/or second shielding appliance 130 such that the healthcare practitioner 10 may manipulate first shielding appliance 120 into a selected position/orientation in the operating environment. For example, the healthcare practitioner 10 may articulate the first shielding appliance 120 into a desired rotational position and/or orientation relative to the patient, base 110, and radiation source 150. The first shielding appliance 120 may include a top edge 121, a bottom edge 122, and side edges 123, 124 and the top edge may be aligned substantially parallel (e.g., parallel or otherwise within 10° of exactly parallel) with an edge 152 of the radiation source 150 when in the selected orientation. Alternatively, the top edge 121 may be angled relative to edge 152 of radiation source 150, such as to align with an angled surface of the patient or other object.

Alternatively, first shielding appliance 120 may be attached to base 110 in a fixed relative position such that first shielding appliance 120 is not adjustable relative to base 110 (e.g., not adjustable by healthcare practitioner 10 in a medical environment at the time of a medical procedure). Such a configuration may facilitate efficient set-up and use by reducing the number of steps performed by healthcare practitioner 10 in the medical environment, and may facilitate efficient manufacturing by reducing the number of parts and assembly steps.

Radiation shielding device 100 is positionable substantially between radiation source 150 and healthcare practitioner 10 to shield healthcare practitioner 10 from radiation. First shielding appliance 120 may extend between a patient and radiation source 150 (e.g., extending along more than 75%, more than 85%, more than 95%, or about 100% of a distance between the patient and a height of radiation source 150). For example, healthcare practitioner 10 may adjust radiation source 150 to a height lower than a height of top edge 121 (FIG. 2) of first shielding appliance 120 (e.g., such that edge 152 of radiation source 150 is located at a height between the patient and top edge 121 of first shielding appliance 120). In this way, first shielding appliance 120 blocks radiation emitted from radiation source 150 beyond the target area and/or radiation reflected towards the doctor by the patient, operating table, floor, etc. Alternatively, or additionally, second shielding appliance 130 may extend from the target area and/or first shielding appliance 120 (e.g., proximate bottom edge 122 of first shielding appliance 120) towards healthcare practitioner 10. In this way, second shielding appliance 130 blocks radiation reflected towards the healthcare practitioner 10 by the patient, operating table, floor, etc.

Healthcare practitioner 10 may arrange multiple radiation shielding devices 100 in close proximity to one another to provide a desired radiation shielding zone A. For example, two radiation shielding devices 100 may be positioned at least partially around a perimeter of radiation source 150 (e.g., in a side-by-side arrangement). Alternatively, or additionally, radiation shielding device 100 may include more than two shielding appliances attached to base 110, such as two shielding appliances 120 extending substantially upwards from base 110 (e.g., two radiation shields 120), and a single shielding appliance 130 extending along a patient away from shielding appliances 120 and radiation source 150 (e.g., a single radiation drape 130). Such a configuration offers healthcare practitioner 10 flexibility and simplicity in arranging radiation shielding device 100 to provide a large radiation shielding zone A to facilitate a particular medical operation, patient anatomy, operating room workflow, or ergonomic preferences, etc.

In an example embodiment, the configuration of radiation shielding device 100 facilitates positioning of the radiation shielding device 100 outside of the target area of radiation source 150. For example, first shielding appliance 120 may extend to a height greater than a lower edge 152 of radiation source 150 (e.g., when radiation source 150 is positioned at an operational distance relative to the patient). Such a height may prevent first shielding appliance 120 from being positioned below radiation source 150 due to physical interference with radiation source 150 that would otherwise occur.

Alternatively, or additionally, second shielding appliance 130 may include a first peripheral edge 134 that is positionable proximate base 110 and/or bottom edge 122 of first shielding appliance 120. In an example embodiment, interference between peripheral edge 134 and one or more features of base 110 provide an indicator of an appropriate position of second shielding appliance 130 relative to base 110 and/or first shielding appliance 120 such that second shielding appliance 130 does not extend substantially beyond first shielding appliance 120 into the target area of radiation source 150 when attached to base 110. For example, when attached to base 110, the second shielding appliance may not extend away from the base on a first side 126 of first shielding appliance 120 (e.g., a first major face 126 oriented towards radiation source 150), and may extend away from the base on a second side 127 of first shielding appliance 120 opposite first side 126. Example radiation shielding device 100 may thus provide a radiation protection zone to shield healthcare practitioner 10 from radiation emitted by radiation source 50 while also promoting a relatively reduced radiation dosage (e.g., a dosage sufficient to perform the medical operation without substantial interference by a shielding appliance in the target area).

Referring now to FIG. 2, an example radiation shielding device 100 and medical device 160 are shown. Radiation shielding device 100 is configured to shield a healthcare practitioner from radiation originating from radiation source 150, while allowing easy manipulation of medical device 160. Medical device 160 may be a tubular medical device, such as a catheter, vascular access sheath, interventional tool, etc., for example.

Medical device 160 passes between first and second sides of radiation shielding device 100, such as between first side 126 proximate a target area of radiation source 150 and a second side 127 opposite the target area (e.g., within a radiation shielding zone provided by radiation shielding device 100). Radiation shielding device 100 is configured to allow medical device 160 to pass between and/or through portions of radiation shielding device 100. In an example embodiment, first shielding appliance 120 includes a slot or notch 125 that provides a space for medical device 160 to pass between first and second shielding appliances 120, 130. For example, slot or notch 125 may be shaped and sized slightly larger than medical device 160 such that medical device 160 may pass through slot or notch 125. Alternatively, slot or notch 125 may be shaped and sized slightly smaller than medical device 160 such that medical device is at least partially constrained within slot or notch 125.

Medical device 160 is positionable relative to radiation shielding device 100 such that a healthcare practitioner may readily manipulate medical device 160 while their hands are protected by first and/or second shielding appliances 120, 130. In an example embodiment, medical device 160 is positionable between first and second shielding appliances 120, 130, such that medical device 160 is above at least a portion of base 110 (e.g., above a platform 111 (FIG. 3) adhered to an object), above second shielding appliance 130 (e.g., resting on second shielding appliance 130), and below first shielding appliance 120. At the location of base 110, for example, the second shielding appliance 130 is positioned above a portion of base 110, the medical device 160 is positioned above second shielding appliance 130 and the portion of base 110, and the first shielding appliance 120 is positioned above medical device 160, second shielding appliance 130, and the portion of base 110. Accordingly, medical device 160 is not below the entire radiation shielding device 100 and is not entirely above the radiation shielding device 100. Such a configuration facilitates manipulation of medical device 160 for efficient operation, while effectively shielding a healthcare practitioner.

Referring now to FIG. 3, an exploded perspective view of example radiation shielding device 100 is shown, including base 110, first shielding appliance 120, and second shielding appliance 130. First and second shielding appliances 120, 130 are attachable to base 110 in a selected orientation/position to provide a radiation shielding zone for a healthcare practitioner. Base 110 includes one or more features that facilitate attachment and or manipulation of first and second shielding appliances 120, 130 (e.g., by a healthcare practitioner in an operating environment).

Base 110 may be configured to attach with first and second shielding appliances 120, 130 such that the first and second shielding appliances 120, 130 may be at least partially retained in a fixed orientation relative to base 110. In an example embodiment, base 110 includes a platform 111 and an articulable mechanism 112 configured to attach first shielding appliance 120 to platform 111. Articulable mechanism 112 includes a pedestal 113, a locking mechanism 114, and a support post 115. Support post 115 includes a ball 115a and an arm 115b. Pedestal 113 and/or locking mechanism 114 define a socket that at least partially accommodates ball 115a. Support post 115 may be articulable to a selected orientation, and retained in the selected orientation (e.g., during a medical operation). In some example embodiments, pedestal 113 and locking mechanism 114 may be joined by complementary threads such that the support post 115 is articulable or more easily articulable when the pedestal 113 and locking mechanism 114 are loosened from one another, and fixed or lease easily articulable when the pedestal 113 and locking mechanism 114 are tightened together. Alternatively, support post 115 and/or first shielding appliance 120 may be articulable and fixed in a selected orientation without manipulation of pedestal 113 or locking mechanism 114, (e.g., such that a healthcare practitioner can move the first shielding appliance 120 into a selected orientation and the first shielding appliance 120 is retained in the selected orientation by friction between pedestal 113, locking mechanism 114, and/or support post 115.

In an example embodiment, second shielding appliance 130 is attachable with platform 111. For example, platform 111 may include an upper surface 111a (e.g., facing first shielding appliance 120). Second shielding appliance 130 may be attachable to upper surface 111a to retain second shielding appliance 130 in a fixed position relative to base 110. In an example embodiment, second shielding appliance 130 may be adhesively attached to base 110. Platform 111 may include an adhesive on at least a portion of upper surface 111a, and a release liner 111b that may be removed to expose the adhesive such that second shielding appliance 130 may be adhered to platform 111. In other example embodiments, second shielding appliance 130 may be attached to platform 111 by hook-and-loop fastener, snap-fits, rivets, etc. Alternatively, or additionally, platform 111 may be supported above second shielding appliance 130. For example, second shielding appliance 130 may be attachable to lower surface 111c of platform 111, and second shielding appliance 130 supported and/or attached to the object (e.g., by an adhesive on a lower surface of second shielding appliance 130).

Second shielding appliance 130 may include one or more features that promote attachment and/or alignment with one or more other features of radiation shielding device 100. For example, second shielding appliance 130 may include a contoured edge 134 that defines a recess or aperture 134a positionable at least partially around a feature of base 110, such as around pedestal 113. Contoured edge 134 may thus facilitate appropriate alignment of second shielding appliance 130 and base 110, and promote intuitive assembly by healthcare practitioner 10 in an operating environment. In an example embodiment, second shielding appliance 130 is non-symmetrical about a center such that contoured edge 134 is shaped differently than perimeter edges 135, 136, 137.

Complementary features of base 110 and second shielding appliance 130, such as contoured edge 134 and pedestal 113, may promote appropriate positioning of radiation shielding device 100 relative to a field of radiation. For example, interference between countered edge 134 of second shielding appliance 130 and base 110 may prevent assembly of second shielding appliance 130 such that second shielding appliance 130 would extend substantially on opposite sides of base 110 and into a target area of radiation (e.g., extend from both sides 126 and 127 of first shielding appliance 120). Second shielding appliance 130 thus extends away from base 110 and first major face 126 of first shielding appliance 120 (e.g., perpendicular to second major face 127, but does not extend away from base 110 and second major face 127 of first shielding appliance 120). Radiation shielding device 100 can be readily assembled such that second shielding appliance 130 extends from base 110 entirely or nearly entirely on second side 127 of first shielding appliance 120, and does not extend from base 110 on first side 126 of first shielding appliance 120 opposite second side 127.

The first and second shielding appliances 120, 130 are positioned above platform 111 when attached to the base 110. For example, the first shielding appliance 120 may extend generally upwards away from platform 111, and the second shielding appliance 130 may extend in a direction generally parallel to a plane defined by platform 111.

At least a portion of second shielding appliance 130 may be arranged parallel with platform 111. For example, second shielding appliance 130 includes an attachment end portion attached to platform 111 such that the second shielding appliance 130 overlaps with platform 111. The overlapping portions of platform 111 and second shielding appliance 130 have a common orientation, and the same orientation relative to first shielding appliance 120. In an example embodiment, platform 111 and at least attachment end portion of second shielding appliance 130 may be arranged perpendicular to first shielding appliance 120. In this way, second shielding appliance may be attached to base 110 while extending across a portion of the patient's body beyond the area of base 110 (e.g., partially above the base 110 and partially beyond the base 110). First shielding appliance 120 may extend upwards from base 110 such that the entire first shielding appliance is at a height greater than the platform 111 and is entirely supported by base 110.

Radiation shielding device 100, including first and second shielding appliances 120, 130 attached to base 110, may be attached to an object. In an example embodiment, radiation shielding device 100 may be adhesively attached to an object. For example, platform 111 of base 110 may include an adhesive on at least a portion of lower surface 111c, and a release liner 111d that may be removed to expose the adhesive such that base 110 may be adhered to an object, second shielding appliance 130, etc. In an example embodiment, release liner 111d may be removed, and platform 111 adhered to an object, before first and second shielding appliances 120, 130 are attached to base 110. Alternatively, platform 111 may be adhered to an object when one or both of first and second shielding appliances 120, 130 are attached to base 110, and/or platform 111 may be attached to second shielding appliance 130 attached to, or otherwise supported on, the object.

In some example embodiments, the only adhesive associated with a surface of second shielding appliance 130 is the adhesive of surface 111a that joins base 110 and second shielding appliance 130. For example, second shielding appliance 130 does not include another adhesive on an outer surface, and is not adhered or otherwise attached to another object (e.g., a patient, surgical draping, etc.). Such a configuration allows efficient and secure positioning via base 110 by a healthcare practitioner in the operating environment.

Alternatively, or additionally, radiation shielding device 100 may include adhesive surfaces only on the top and/or bottom of platform 111. For example, upper surface 111a, lower surface 111c, or both upper surface 111a and lower surface 111c may be the only adhesive surfaces of radiation shielding device 100. Such a configuration provides a simply construction that is readily assembled and positioned by a healthcare practitioner in the operating environment.

Platform 111 and/or other components of base 110 may be configured to promote stability and secure attachment to an object. In an example embodiment, platform 111 may be made from a flexible material, such as a foam, that allows platform 111 to conform to the contour of an object it is attached to. In some embodiments, platform 111 may be made from a malleable material, and/or include a malleable frame or wire, such that platform 111 at least partially retains its shape when flexed. In an example embodiment, platform 111 is made from a material that has substantially lower radiation shielding properties compared to first and second shielding appliances 120, 130. Such a configuration may facilitate a relatively large platform that provides a large surface area to contact a supporting object and or for attachment with first and second shielding appliances 120, 130, without substantially interfering with radiation source 150 if positioned proximate a target area. In other example embodiments, platform 111 may be made from a radiation shielding material that provides a level of radiation shielding similar to first and/or second shielding appliances 120, 130.

In some embodiments, platform 111 may have a laminated multi-layer construction that includes one or more foam layers and a reinforcing layer (e.g., of metal or plastic). Platform 111 may be made from biocompatible metallic or polymeric material, such as a medical grade foam. The adhesives of base 110 may be medical grade adhesive that is resistant to fluids that may be encountered in a medical environment, such as water, blood, bodily fluids, etc. Alternatively, or additionally, base 110 may include one or more other attachment mechanisms, such as a suction device, adjustable strap system, hook-and-loop fastener, snap-fit, sleeve positionable around a portion of a patient's body (e.g., arm or leg).

In an example embodiment, first shielding appliance 120 is a substantially rigid, shape-stable radiation shield (e.g., that maintains a predefined shape under the force of gravity), and second shielding appliance 130 is relatively more flexible and/or non-shape stable (e.g., such that second shielding appliance 130 may deform or bend under the force of gravity). For example, second shielding appliance 130 may be a flexible radiation shielding drape that may at least partially conform to a surface or object that second shielding appliance 130 is supported on.

In some embodiments, first shielding appliance 120 includes one or more layers of radiation shielding material, such as a sheet of lead or other heavy metal. The radiation shielding material may be laminated or otherwise positioned between outer plastic or metal layers. Alternatively, or additionally, first shielding appliance 120 may be fabricated from a polymeric material infused with one or more materials that sufficiently block radiation to provide a zone of safe radiation levels, such as barium, tin, aluminum, tungsten, lead, other attenuating metal, etc.).

In some embodiments, second shielding appliance 130 includes a flexible radiation shielding drape. Second shielding appliance 130 may include one or more layers of radiation shielding material, such as lead or other heavy metal, covered by a polymer, fabric, or non-metallic outer layer. In various example embodiments, second shielding appliance 130 may include one or more of barium, tin, aluminum, tungsten, lead, other attenuating metal, etc. The radiation shielding materials of second shielding appliance 130 thus provide sufficient radiation blocking to provide a zone of safe radiation levels.

First shielding appliance 120 may differ from second shielding appliance 130 in one or more characteristics. For example, first shielding appliance 120 may be relatively more rigid and second shielding appliance 130 may be relatively more flexible. First shielding appliance 120 may be relatively less thick and second shielding appliance 130 may be relatively thicker (e.g., second shielding appliance 130 may have a thickness that is two, three, or more times that of the thickness of first shielding appliance 120). First shielding appliance 120 may have a surface area that is smaller than a surface area of second shielding appliance 130 (e.g., second shielding appliance 130 may have a surface area that is two, three, four, five, or more times that of the surface area of first shielding appliance 120). First shielding appliance 120 may have a weight that is less than a weight of second shielding appliance 130.

The size of first shielding appliance 120 may be different than the size of second shielding appliance 130. In an example embodiment, a width of first shielding appliance 120 (e.g., between side edges 123 and 124) is less than a width of second shielding appliance 130 (e.g., between edges 135 and 136 in an expanded configuration), and a height of first shielding appliance 120 (e.g., between top edge 121 and bottom edge 122) is less than a length of second shielding appliance 130 (e.g., between edges 134 and 137 in an expanded configuration).

Radiation shielding device 100 may be received by a healthcare practitioner as a sterile kit, such that one or more components of radiation shielding device 100 can be removed from sterile packaging and positioned for use within the medical environment. In some example embodiments, a radiation shielding device kit may include multiple disposable bases 110 and disposable second radiation shielding appliances 130 (e.g., non-shape-stable radiation shielding drapes) that can be used with a single, sterilizable, first radiation shielding appliance 120 (e.g., shape-stable radiation shield).

Figure 4:
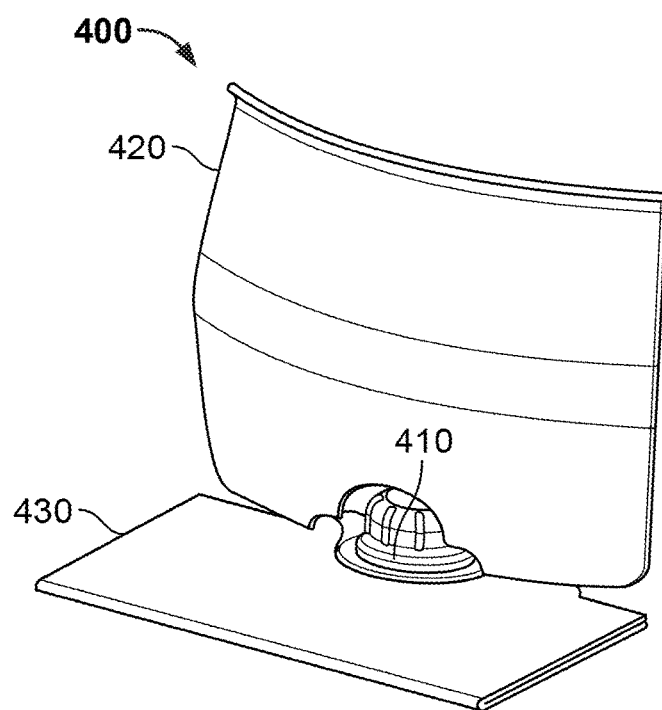
FIG. 4 is a perspective view of an example radiation shielding device.
Figure 5:
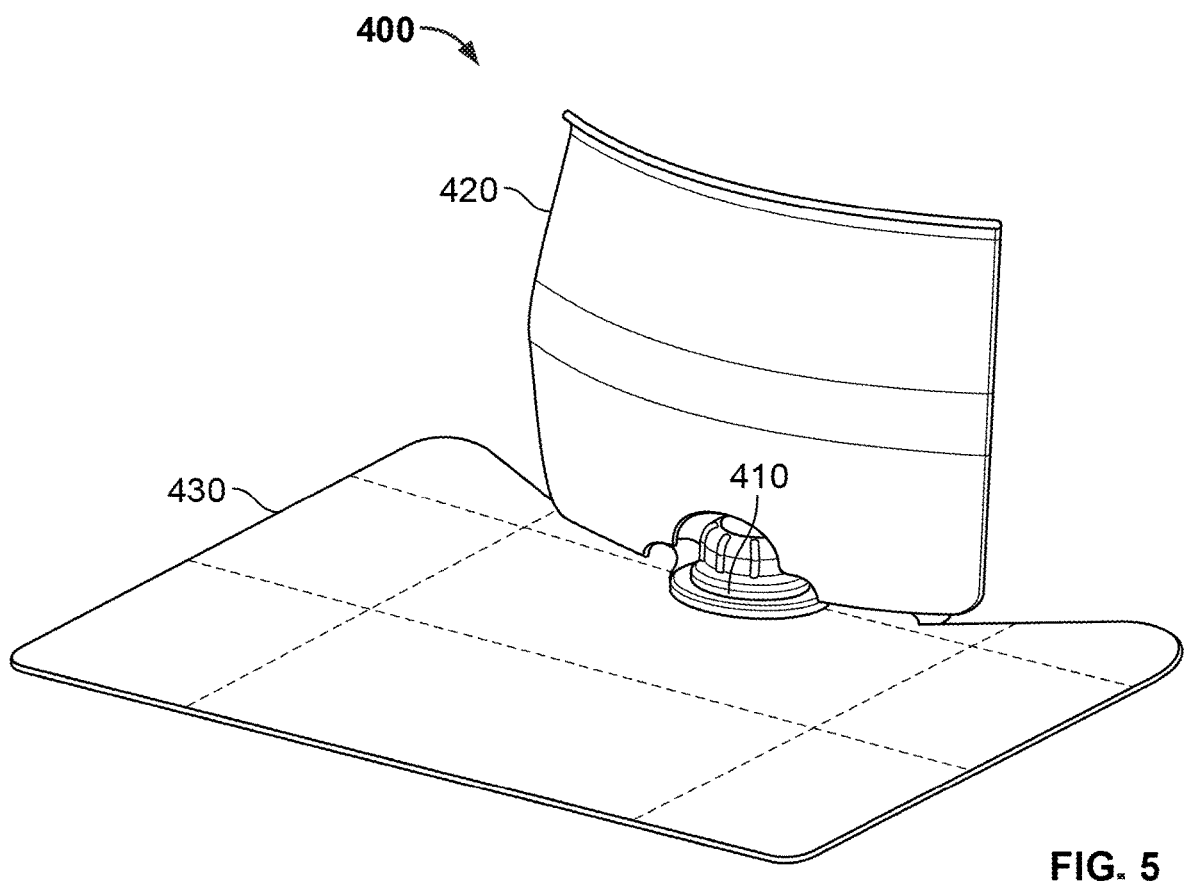
FIG. 5 is a perspective view of the example radiation shielding device of FIG. 4 having a shielding appliance in an extended configuration.

Referring now to FIGS. 4 and 5, an example radiation shielding device 400 is shown, including a base 410, first shielding appliance 420, and second shielding appliance 430. In various example embodiments, radiation shielding device 400 may include one or more features as described herein with reference to radiation shielding device 100.

Second shielding appliance 430 may be operable between a folded or contracted configuration (FIG. 4) and an unfolded or expanded condition (FIG. 5). In an example embodiment, second shielding appliance 430 is at least partially rolled or folded over itself in the folded or contracted configuration (e.g., before removal from sterile packaging at a time of use). A thickness in the folded or contracted configuration may be double, triple, or more than a thickness in the unfolded or expanded condition. In the folded or expanded condition (FIG. 5), the second shielding appliance 430 may be partially or entirely expanded to provide an increased coverage area as compared to the folded or contracted configuration.

Second shielding appliance 430 may be adjusted by a healthcare practitioner during assembly and set-up of radiation shielding device 400. In an example embodiment, a healthcare practitioner may adjust second shielding appliance 430 from the folded or contracted configuration to the unfolded or expanded configuration while first and second shielding appliances 420, 430 are attached to base 410. Alternatively, second shielding appliance 430 may be unfolded or expanded before first shielding appliance 420 and/or second shielding appliance 430 are attached to base 410.

A folded or contracted configuration provides a relatively small size that promotes efficient packaging and handling of second shielding appliance 430. For example, in the folded or contracted configuration, second shielding appliance 430 may have an outer surface area that is less than double, the same, or less than the outer surface area of first shielding appliance 420. In the unfolded or expanded configuration, second shielding appliance 430 may have an outer surface area that is greater than the outer surface area of the first shielding appliance 420, such as more than two, three, four, or more times the outer surface area of the first shielding appliance 420.

Adjustment between the folded or contracted configuration may allow a healthcare practitioner to position second shielding appliance 430 with a selected footprint on an object (e.g., a desired coverage area on a patient). Second shielding appliance 430 thus may provide variable coverage with a single device. Alternatively, or additionally, adjustment between the folded or contracted configuration and the unfolded or expanded configuration allows a variable degree of radiation shielding, such as to provide an increased degree of shielding in areas of greater thickness where the material of second shielding appliance 430 is folded about itself, and a reduced degree of shielding in areas of reduced thickness where the material of second radiation shielding appliance 430 is not folded about itself.

Figure 6:
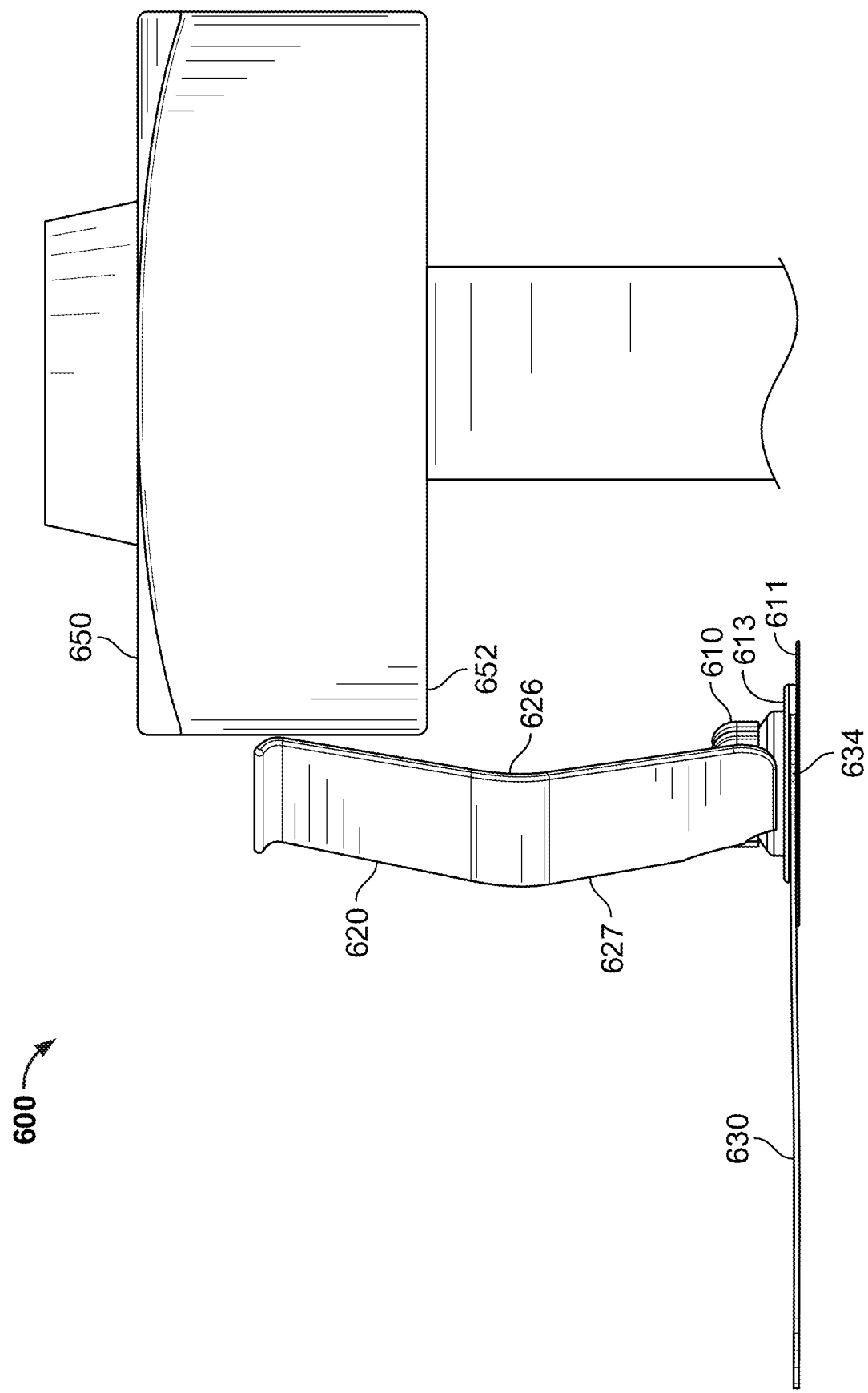
FIG. 6 is a side view of an example radiation shielding device and radiation source.
Figure 7:
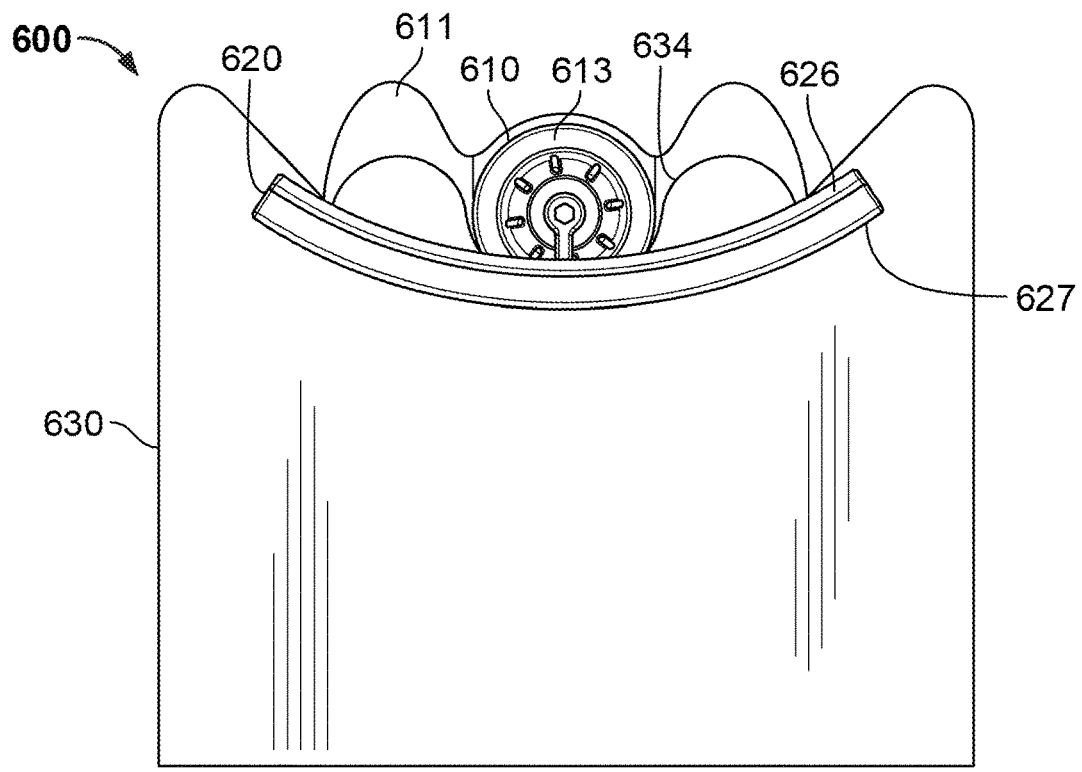
FIG. 7 is a top view of the example radiation shielding device of FIG. 6.
Figure 8:
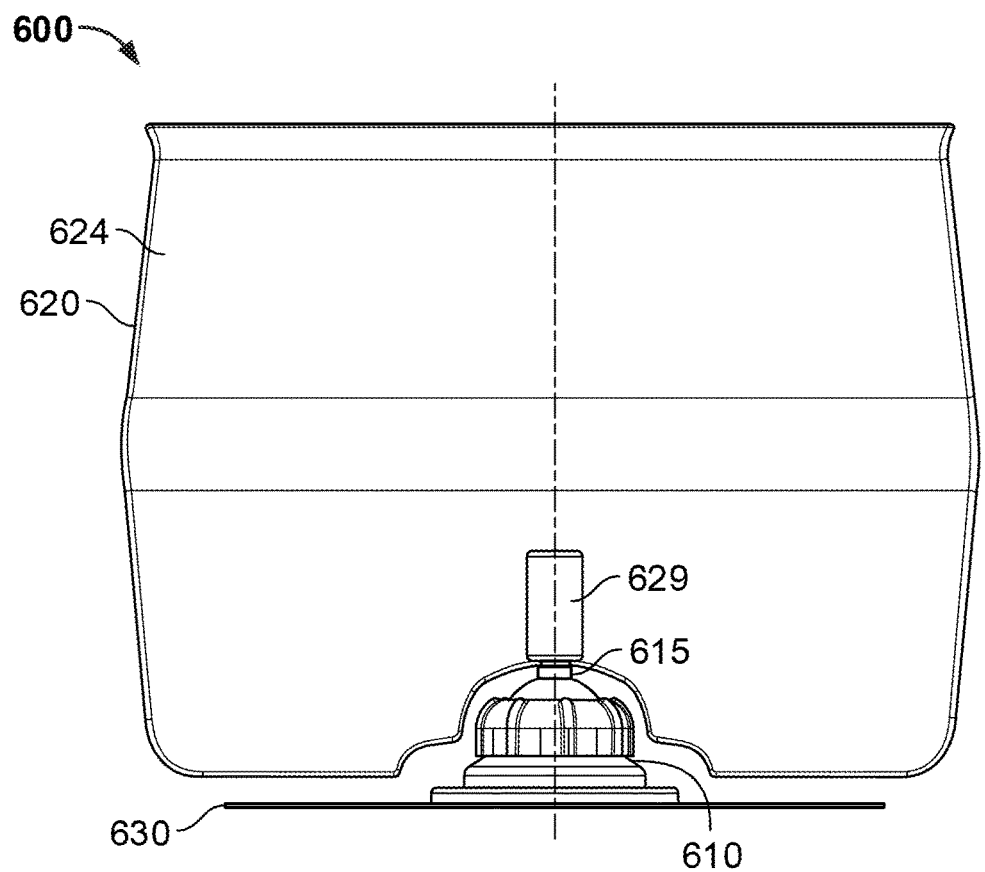
FIG. 8 is a rear view of the example radiation shielding device of FIG. 6.

Referring now to FIGS. 6-8, an example radiation shielding device 600 is shown, including a base 610, first shielding appliance 620, and second shielding appliance 630. In various example embodiments, radiation shielding device 600 may include one or more features as described herein with reference to radiation shielding devices 100 and 400.

In an example embodiment, first shielding appliance 620 extends between an object supporting radiation shielding device 600 and a radiation source 650 (e.g., entirely between the object and edge 652 of radiation source 650), and second shielding appliance 630 extends away from base 610 and first shielding appliance 620 substantially on a second side 627 of first shielding appliance 620 opposite from a first side 626 that faces towards radiation source 650. For example, more than 75%, more than 85%, more than 95%, or more of second shielding appliance 630 is positioned on the second side 627 of first shielding appliance 620 (e.g., to the left of first shielding appliance 620 in the view shown in FIG. 6). Such a configuration reduces potential interference with the target area of the radiation field emitted by radiation source 650 that may otherwise result if second shielding appliance 630 were positioned over the target area.

In some embodiments, platform 611 of base 610 extends a greater distance from a second side 627 of first shielding appliance 620 than the second shielding appliance 630 (FIGS. 6 and 7). In an example embodiment, platform 611 is substantially radio transparent relative to second shielding appliance 630 and does not substantially interfere with radiation emitted by radiation source 650. In some embodiments, platform 611 is substantially radio transparent relative to second shielding appliance 630 on a portion extending towards a radiation target area on first side 626 of first shielding appliance 620, and substantially radio opaque on a portion extending away from the radiation target area on second side 627. Second shielding appliance 630 includes a contoured edge 634 having one or more features that interact with one or more complementary features of base 610. The countered edge may be configured to extend at least partially around a portion of base 610, such as pedestal 613, while not extending beyond platform 611. Such a configuration may promote a relatively large area of contact between base 610 and second shielding appliance 630 while second shielding appliance 630 is prevented from extending into or otherwise interfering with the field of radiation on second side 627 of first shielding appliance 620.

Referring now to FIG. 8, second radiation appliance 630 may include one or more features compatible with base 610. In an example embodiment, a protrusion 629 extends from first side 626 of first shielding appliance 620. Protrusion 629 that may interact with mechanism 112 to support and/or secure first shielding appliance 620 in a desired orientation relative to base 610. For example, protrusion 629 may define a non-circular or keyed opening that receives a post 615 of base 610.

Figure 9:
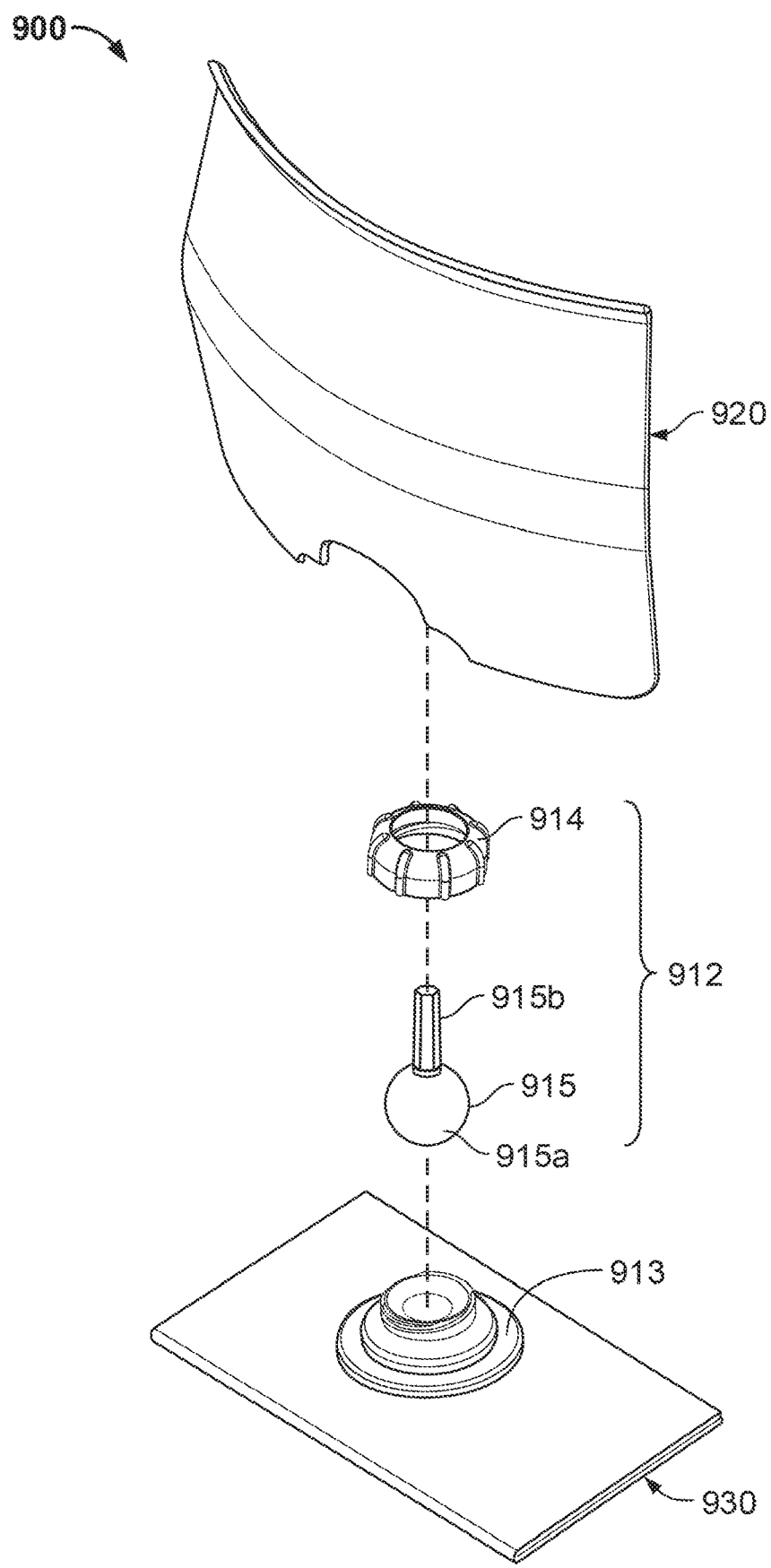
FIG. 9 is an exploded view of an example radiation shielding device.
Figure 10:
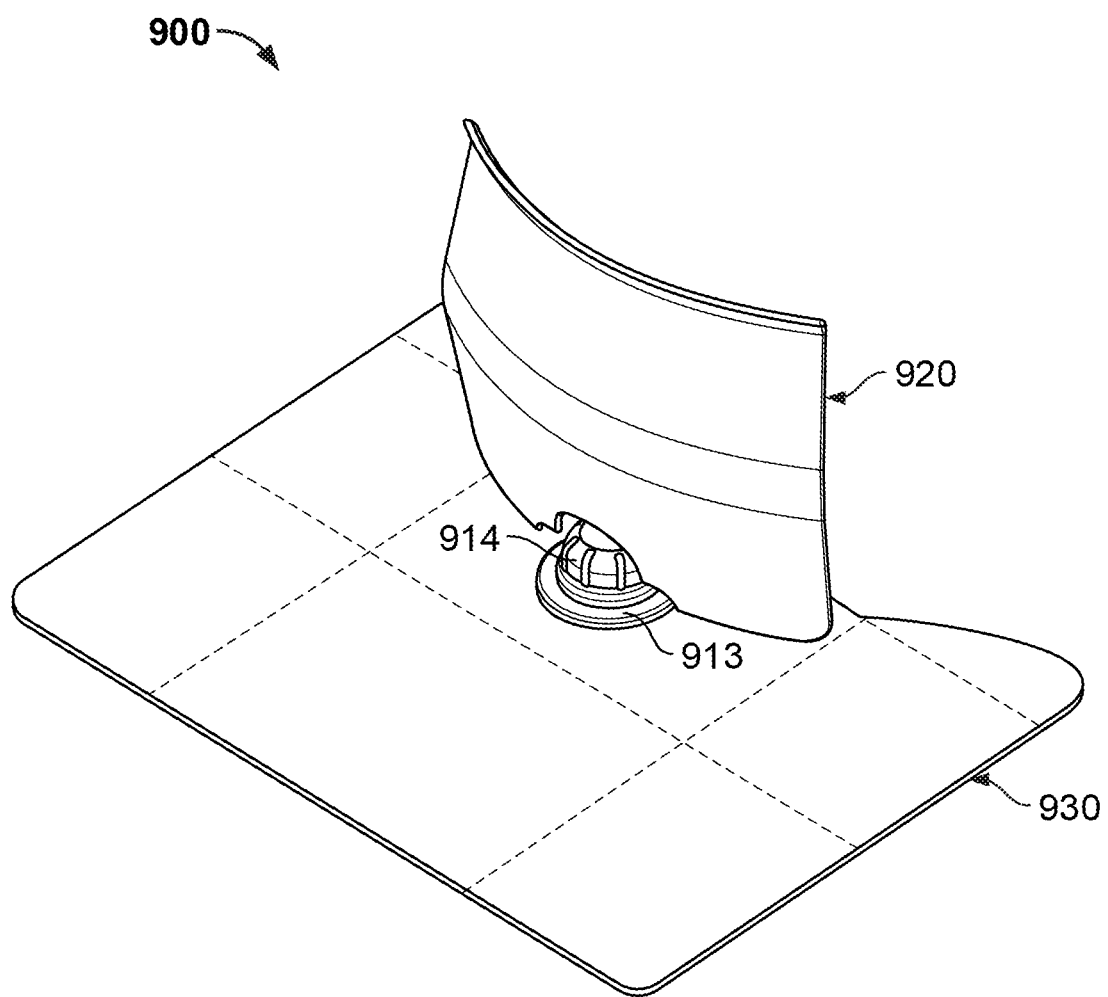
FIG. 10 is a perspective view of the example radiation shielding device of FIG. 9, having a shielding appliance in an extended configuration.

Referring now to FIGS. 9 and 10, an example radiation shielding device 900 is shown, including first shielding appliance 920 and second shielding appliance 930. First and second radiation appliances 920, 930 are attached to one another by an articulable mechanism 912. In various example embodiments, radiation shielding device 900 may include one or more features as described herein with reference to radiation shielding devices 100, 400, and 600.

Articulable mechanism 912 may be configured to attach first shielding appliance 920 to second shielding appliance 930 such that first shielding appliance 920 may be articulated relative to second shielding appliance 930. In an example embodiment, articulable mechanism 912 includes a pedestal 913, a locking mechanism 914, and a support post 915. Support post 915 includes a ball 915*a* and an arm 915*b*. Pedestal 913 and/or locking mechanism 914 define a socket that at least partially accommodates ball 915*a*. Support post 915 may be articulable to a selected orientation, and retained in the selected orientation (e.g., during a medical operation).

In some example embodiments, pedestal 913 and locking mechanism 914 may be joined by complementary threads such that the support post 915 is articulable or more easily articulable when the pedestal 913 and locking mechanism 914 are loosened from one another, and fixed or lease easily articulable when the pedestal 913 and locking mechanism 914 are tightened together. Alternatively, support post 915 and/or first shielding appliance 920 may be articulable and fixed in a selected orientation without manipulation of pedestal 913 or locking mechanism 914, (e.g., such that a healthcare practitioner can move the first shielding appliance 920 into a selected orientation and the first shielding appliance 920 is retained in the selected orientation by friction between pedestal 913, locking mechanism 914, and/or support post 915).

In an example embodiment, pedestal 913 is directly connected to second shielding appliance 930 (e.g., via adhesive, welding, etc., or integrally formed with second shielding appliance 930). For example, radiation shielding device 900 does not include an additional platform attachable to an object and to which the first and second shielding appliances are each attached to.

Second shielding appliance 930 may be supported directly by an object, such as a patient such as a patient's skin, clothing, surgical draping, table, bed rail, etc. In an example embodiment, the weight of second shielding appliance 930 provides sufficient stability to support first shielding appliance in a desired position during a medical operation, and radiation shielding device 900 does not include adhesive or other attachment mechanism to attach radiation shielding device 900 to the object. Alternatively, or additionally, radiation shielding device 900 may be attached to the object by adhesive, hook-and-loop, etc. on a bottom surface of second shielding appliance 930.

Second shielding appliance 930 may be operable between a folded or contracted configuration (FIG. 9) and an unfolded or expanded condition (FIG. 10). In an example embodiment, second shielding appliance 930 is at least partially rolled or folded over itself in the folded or contracted configuration (e.g., before removal from sterile packaging at a time of use). A thickness in the folded or contracted configuration may be double, triple, or more than a thickness in the unfolded or expanded condition. In the folded or expanded condition, the second shielding appliance 930 may be partially or entirely expanded to provide an increased coverage area as compared to the folded or contracted configuration.

A folded or contracted configuration provides a relatively small size that promotes efficient packaging and handling of second shielding appliance 930. For example, in the folded or contracted configuration, second shielding appliance 930 may have an outer surface area that is less than double, the same, or less than the outer surface area of first shielding appliance 920. In the unfolded or expanded configuration, second shielding appliance 930 may have an outer surface area that is greater than the outer surface area of the first shielding appliance 920, such as more than two, three, four, or more times the outer surface area of the first shielding appliance 920.

Adjustment between the folded or contracted configuration may allow a healthcare practitioner to position second shielding appliance 930 with a selected footprint on an object (e.g., a desired coverage area on a patient). Second shielding appliance 930 thus may provide variable coverage with a single device. Alternatively, or additionally, adjustment between the folded or contracted configuration and the unfolded or expanded configuration allows a variable degree of radiation shielding, such as to provide increased shielding in areas of greater thickness where the material of second shielding appliance 930 is folded about itself, and reduced shielding in areas of reduced thickness where the material of second radiation shielding appliance 930 is not folded about itself.

Figure 11:
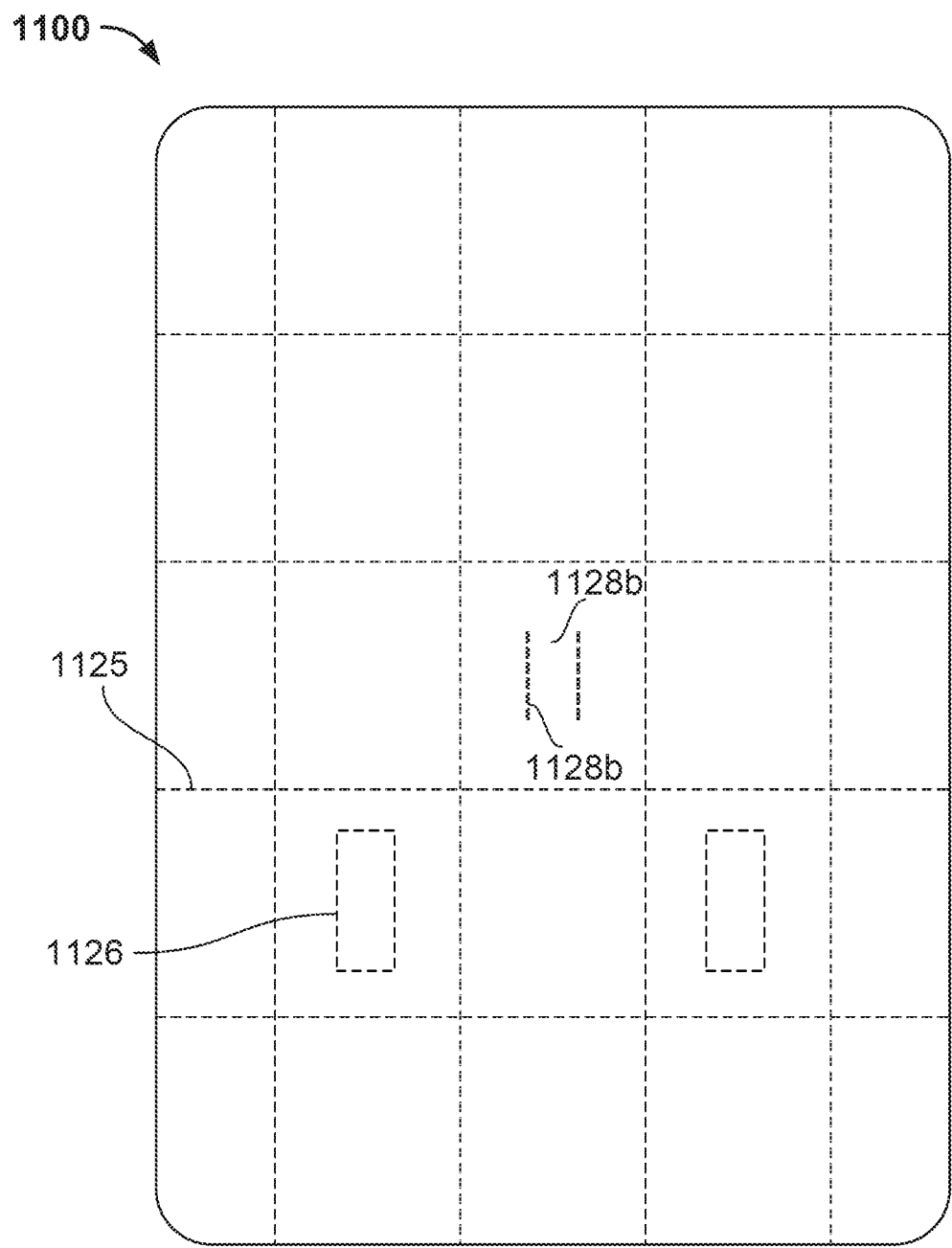
FIG. 11 is a front view of an example radiation shielding device in a first configuration.
Figure 12:
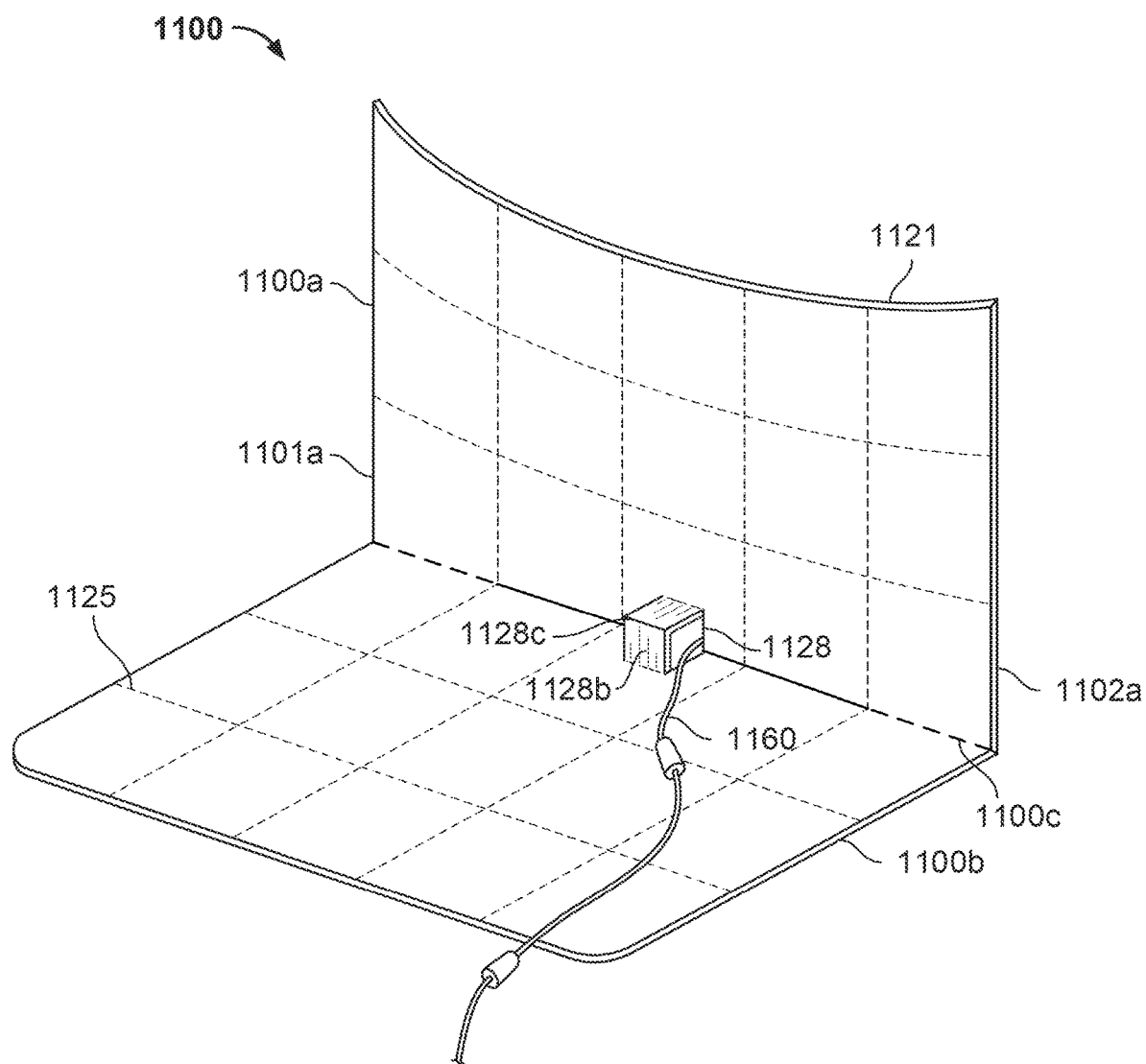
FIG. 12 is a perspective view of the example radiation shielding device of FIG. 11 in a second configuration.

Referring now to FIGS. 11 and 12, an example radiation shielding device 1100 is shown. Radiation shielding device 1100 may be manipulated into a user selected configuration, such as a configuration that provides radiation shielding in substantially horizontal and substantially vertical orientations. In various example embodiments, radiation shielding device 1100 may include one or more features as described herein with reference to radiation shielding devices 100, 400, 600, and 900.

In an example embodiment, radiation shielding device 1100 may be manipulated by a healthcare practitioner into a configuration including two or more portions angled relative to one another (FIG. 12). For example, radiation shielding device 1100 may be folded such that a first portion 1100a of the radiation shielding device 1100 is in a substantially vertical orientation and the second portion 1100b of the radiation shielding device is in a substantially horizontal orientation. The first portion 1100a and the second portion 1100b may thus form an angle between about 135° and 45°, 105° and 75°, or about 90°. In some embodiments, the angle is an overall relative orientation of the first and second portions 1100a, 1100b, while the first and/or second portions 1100a, 1100b may have non-planar portions or discrete surfaces of varying relative orientations.

Alternatively, or additionally, radiation shielding device 1100 may be manipulated to impart a selected curvature. For example, a top edge 1121 may exhibit a curvature to at least partially surround a radiation field, target area or a patient, etc. One or more portions may be manipulated to impart a complex curvature such that radiation shielding device 1100 is curved about multiple axes. A healthcare practitioner may thus manipulate radiation shielding device 1100 into a selected configuration based on one or more of the healthcare practitioner's preferences, the medical procedure being performed, the medical tools being used, the location of the procedure, the anatomy of the patient, etc. A radiation shielding device 1100 having first and second portions angled relative to one another, such as in substantially horizontal and substantially vertical orientations, may provide a relatively large zone of protection from direct and scatter radiation.

In an example embodiment, first and second portions 1100a, 1100b, are integrally formed as a unitary component. One or more layers of radiation shielding device 1110 may be present in both first and second portions 1100a, 1100b. The first and second portions 1100a, 1100b may be uninterrupted by separations, gaps, openings, etc., across at least a portion of a width of radiation shielding device 1100. In this way, radiation shielding device 1100 may promote a consistent zone of protection for a healthcare practitioner.

Radiation shielding device 1100 may include a slit, separation, slot, etc., such as slit 1100c, at which first shielding portion 1100a is separated from other portions of radiation shielding device 1100 (e.g., such as second shielding portion 1100b). Slit 1100c may provide additional mobility of first shielding portion 1100a independent of second shielding portion 1100b, or vice versa, for example. A healthcare may position first shielding portion 1100a, such as by rotating first shielding portion 1100a, manipulating edges 1101a, 1102a, etc., while being less constrained (e.g., as compared to if slit 1100c were not present). In this way, radiation shielding device 1100 may provide additional flexibility for a healthcare practitioner to manipulate radiation shielding device 1100 into a selected position.

In some embodiments, radiation shielding device 1100 includes one or more layers of radiation shielding material, such as a sheet of lead or other heavy metal. The radiation shielding material may be laminated or otherwise positioned between outer fabric, plastic, or metal layers. Alternatively, or additionally, radiation shielding device 1100 may include a polymeric material infused with one or more materials that sufficiently block radiation to provide a zone of safe radiation levels, such as barium, tin, aluminum, tungsten, lead, other attenuating metal, etc.).

At least portions of radiation shielding device 1100 may be made from a conformable, shape-stable material such that the radiation shielding device 1100 can maintain itself in a selected configuration. For example, radiation shielding device 1100 may be manipulated by a healthcare practitioner from a planar configuration (FIG. 11) to a folded configuration (FIG. 12), and may maintain the folded configuration during a medical operation or until further manipulated by the healthcare practitioner. In various example embodiments, radiation shielding device 1100 may include a frame 1125, including a plurality of wires or conformable structural support elements that are malleable and contribute to maintaining radiation shielding device 1100 in a selected configuration. In some embodiments, internal frame 1125 may include a sheet or planar layer of malleable material. Alternatively, or additionally, one or more layers of radiation shielding device 1100 may provide both structural support and substantial radiation shielding. In some example embodiments, radiation shielding device 1100 may include bendable wires, bendable rods, bendable stiffened sheets, bendable tubes, gas or liquid inflatable channels, etc. that impart structure and contribute to maintaining radiation shielding device 1100 in a selected configuration.

Radiation shielding device 1100 may include one or more attachment locations 1126 that facilitate stable support on an object, such as a patient, patient's skin, clothing, surgical draping, table, bed rail, etc. In an example embodiment, attachment locations 1126 include an adhesive, hook-and-loop fastener, etc. that may be releasably attached to the object. Alternatively, or additionally, the weight of radiation shielding device 1100 may promote stability to support radiation shielding device 100, including a substantially vertical portion 1100b extending upwardly from the surface, in a desired position during a medical operation. In some example embodiments, radiation shielding device 1100 does not include adhesive or other attachment mechanism to attach radiation shielding device 1100 to the object. Likewise, in some example embodiments, radiation shielding device does not include a base, and may be directly attached or supported by the object.

Radiation shielding device 1100 may be configured to shield a healthcare practitioner while allowing a medical device 1160 to pass between opposite sides of radiation shielding device 1100. In an example embodiment, radiation shielding device 1100 includes a passage 1128 defined through an entire thickness of radiation shielding device 1100. The medical device 1160 may extend through the radiation shielding device 1100. A healthcare practitioner may readily manipulate medical device 1160 while their hands are within the zone of protection provided by radiation shielding device 1100. In various example embodiments, medical device 1160 may be a tubular medical device, sheath, interventional tool, or other device.

Passage 1128 may be defined by one or more slits 1128a through the thickness of radiation shielding device 1100. A portion of material 1128b between first and second slits 1128a may be folded or popped outwardly such that medical device 1160 may pass through radiation shielding device 1100. In some embodiments, a preformed fold line 1128c may facilitate folding of material 1128b when radiation shielding device 1100 is manipulated into a selected configuration. The portion of material 1128b may be pushed toward medical device 1160, for example, to substantially close passage 1128. The portion of material 1128b may contact medical device 1160 so that little or no gap is present between medical device 1160, material 1128b, and/or other material of radiation shielding device 1100. In various embodiments, such a configuration facilitates passage of medical device 1160 through radiation shielding device 1100 while promoting a consistent and uninterrupted zone of protection for the healthcare practitioner. Alternatively, passage 1128 may be omitted, and medical device 1160 may pass through slit 1100c, for example.

Figure 13:
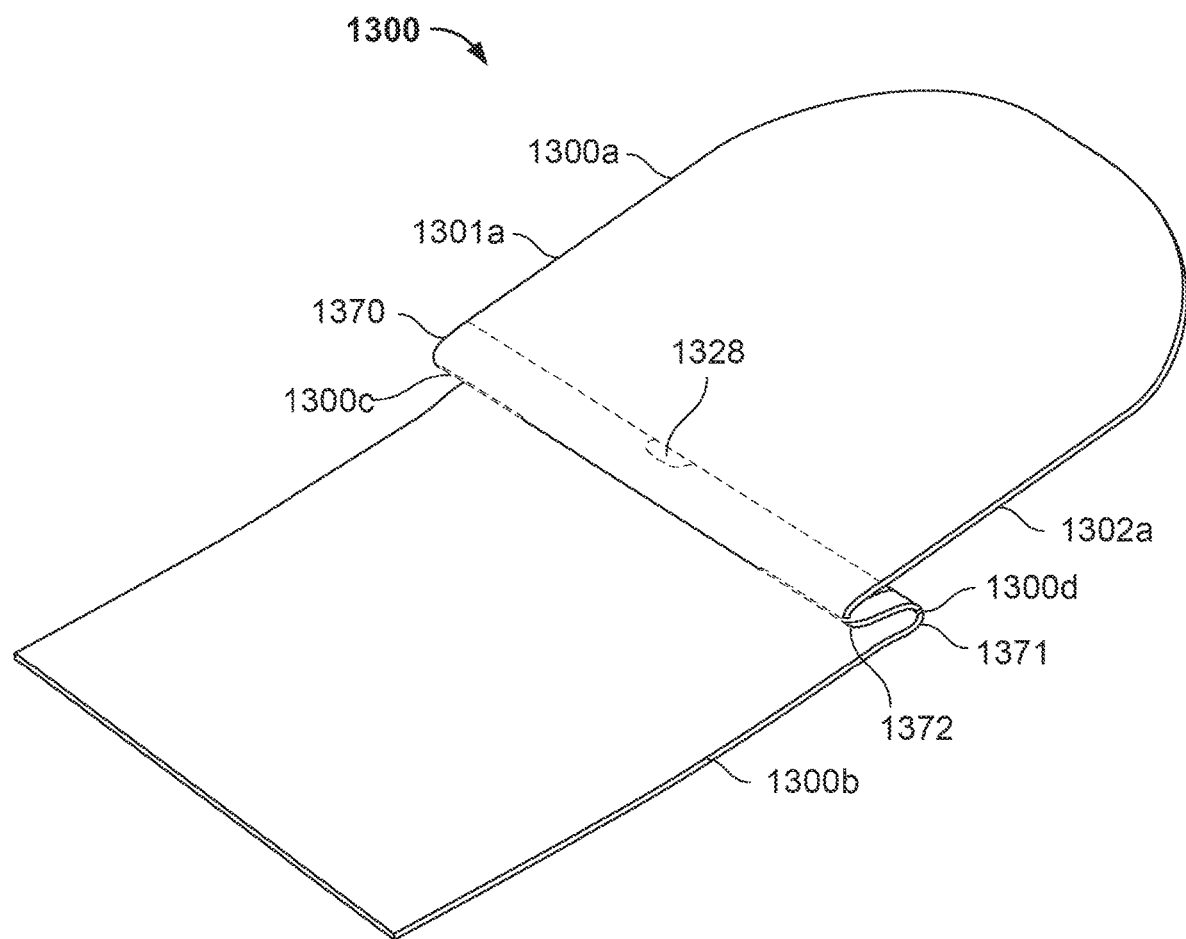
FIG. 13 is a perspective view of an example radiation shielding device in a first configuration.
Figure 14:
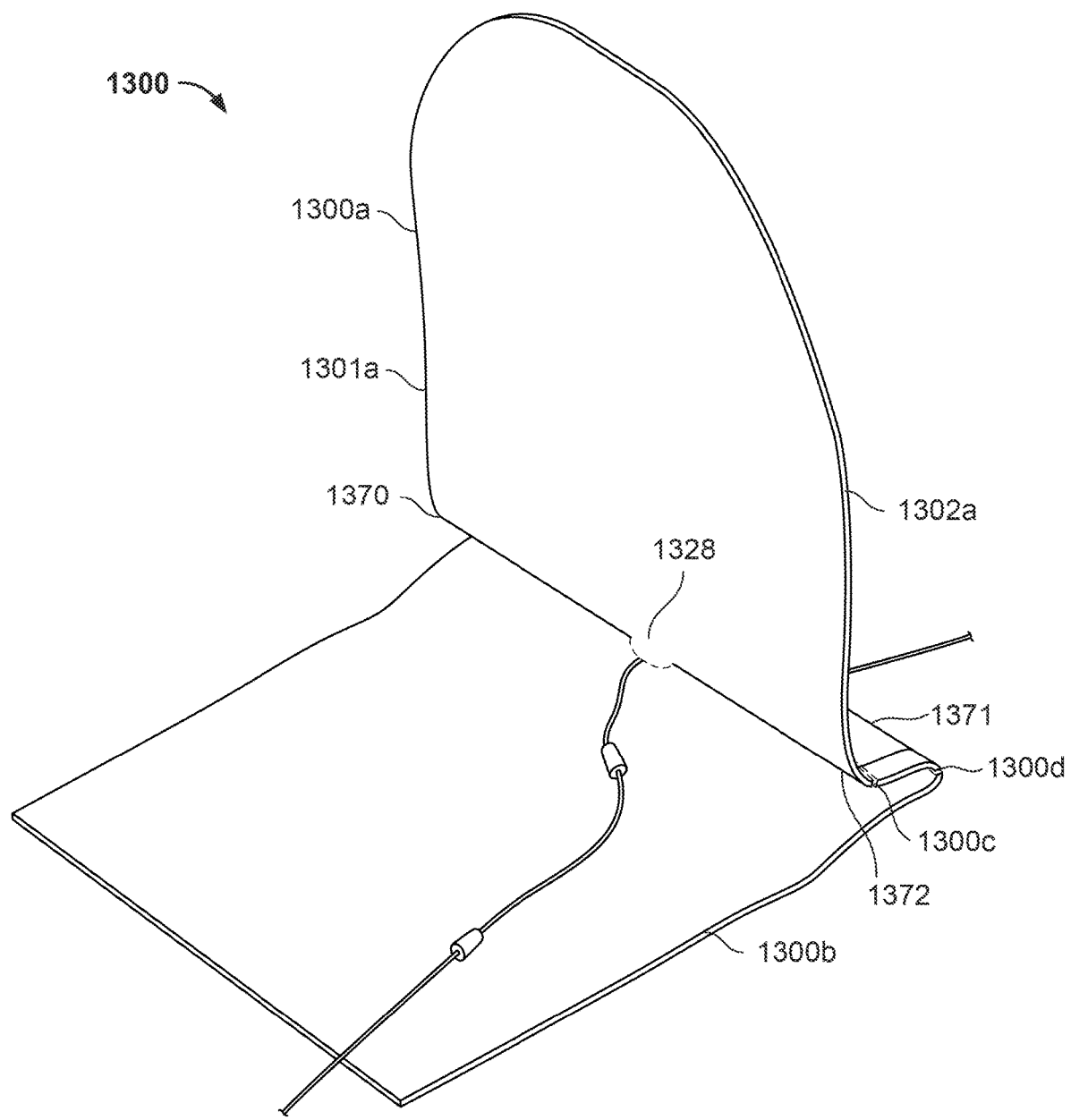
FIG. 14 is a perspective view of an example radiation shielding device in a second configuration.

Referring now to FIGS. 13 and 14, an example radiation shielding device 1300 is shown. Radiation shielding device 1300 includes a folded region 1370 and may be manipulated into a user selected configuration, such as a configuration that provides radiation shielding in substantially horizontal and substantially vertical orientations. In various example embodiments, radiation shielding device 1300 may include one or more features as described herein with reference to radiation shielding devices 100, 400, 600, 900, and 1100.

In an example embodiment, radiation shielding device 1300 includes a folded region 1370 between two or more radiation shielding portions. Radiation shielding device 1300 may be manipulated between a first configuration (FIG. 13) including folded region 1370 in which radiation shielding device 1300 is in a substantially planar configuration (e.g., in which an angle between the first shielding portion and the second shielding portion is between 0° and 195°), and a second configuration in which a first portion 1300a of the radiation shielding device 1300 is in a substantially vertical orientation and the second portion 1300b of the radiation shielding device is in a substantially horizontal orientation (FIG. 14). Folded region 1370 may be provided by a healthcare practitioner, such as by imparting first and second fold locations 1371 and/or 1372. Alternatively, or additionally, fold locations 1371 and/or 1372 may be imparted at a time of manufacturing. In some example embodiments, the healthcare practitioner may receive radiation shielding device 1300 preconfigured to have folded region 1370 (e.g., including first and second fold locations 1371 and 1372), and may manipulate first portion 1300a into a selected position relative to second portion 1300b.

In various selected orientations, the first portion 1300a and the second portion 1300b may form an angle between about 135° and 45°, 105° and 75°, or about 90° (e.g., in the second configuration). In some embodiments, the angle is an overall relative orientation of the first and second portions 1300a, 1300b, while the first and/or second portions 1300a, 1300b may have non-planar portions or discrete surfaces of varying relative orientations.

Alternatively, or additionally, one or more portions may be manipulated to impart a complex curvature such that radiation shielding device 1300 is curved about multiple axes. A healthcare practitioner may thus manipulate radiation shielding device 1300 into a selected configuration based on one or more of the healthcare practitioner's preferences, the medical procedure being performed, the medical tools being used, the location of the procedure, the anatomy of the patient, etc. A radiation shielding device 1300 having first and second portions angled relative to one another, such as in substantially horizontal and substantially vertical orientations, may provide a relatively large zone of protection from direct and scatter radiation.

In an example embodiment, first and second portions 1300a, 1300b, are integrally formed as a unitary component. One or more layers of radiation shielding device 1310 may be present in both first and second portions 1300a, 1300b. The first and second portions 1300a, 1300b may be uninterrupted by separations, gaps, openings, etc., across at least a portion of a width of radiation shielding device 1300. In this way, radiation shielding device 1300 may promote a consistent zone of protection for a healthcare practitioner.

Radiation shielding device 1300 may include a slit, separation, slot, etc., such as slit 1300c, at which first shielding portion 1300a is separated from other portions of radiation shielding device 1300 (e.g., such as second shielding portion 1300b), and/or slit 1300d, at which second shielding portion 1300b is separated from other portions of radiation shielding device 1300 (e.g., such as first shielding portion 1300a). In an example embodiment, slit 1300c is parallel and/or collinear with first fold location 1372, and/or slit 1300d is parallel and/or collinear with second fold location 1372. Slits 1300c, 1300d may provide additional mobility of first shielding portion 1300a independent of second shielding portion 1300b, or vice versa, for example. A healthcare may position first shielding portion 1300a, such as by rotating first shielding portion 1300a, manipulating edges 1301a, 1302a, etc., while being less constrained (e.g., as compared to if slit 1300c and/or slit 1300d were not present). In this way, radiation shielding device 1300 may provide additional flexibility for a healthcare practitioner to manipulate radiation shielding device 1300 into a selected position.

In various exemplary embodiments, slits 1300c, 1300d, may be present along about 80% of the total width of first and/or second radiation shielding portions 1300a, 1300b. For example, slits 1300c, 1300d, may be present between about 20% to 90%, 50% to 85%, or 60% to 80% of the total width of first and/or second radiation shielding portions 1300a, 1300b. Such dimensions may impart adjustability while providing adequate structural support (e.g., for first shielding portion 1300a that may be positioned in a substantially vertical orientation relative to second shielding portion 1300b).

In some embodiments, radiation shielding device 1300 includes one or more layers of radiation shielding material, such as a sheet of lead or other radiation blocking metal. The radiation shielding material may be laminated or otherwise positioned between outer fabric, plastic, or metal layers. Alternatively, or additionally, radiation shielding device 1300 may include a polymeric material infused with one or more materials that sufficiently block radiation to provide a zone of safe radiation levels, such as barium, tin, aluminum, tungsten, lead, other attenuating metal, etc.).

At least portions of radiation shielding device 1300 may be made from a conformable, shape-stable material such that the radiation shielding device 1300 can maintain itself in a selected configuration. For example, radiation shielding device 1300 may be manipulated by a healthcare practitioner from a planar configuration (FIG. 13) to an angled configuration (FIG. 14), and may maintain the angled configuration during a medical operation or until further manipulated by the healthcare practitioner.

Radiation shielding device 1300 may be configured to shield a healthcare practitioner while allowing a medical device 1360 to pass between opposite sides of radiation shielding device 1300. In an example embodiment, radiation shielding device 1300 includes a passage 1328 defined through an entire thickness of radiation shielding device 1300. The medical device 1360 may extend through the radiation shielding device 1300. A healthcare practitioner may readily manipulate medical device 1360 while their hands are within the zone of protection provided by radiation shielding device 1300. In various example embodiments, medical device 1360 may be a tubular medical device, sheath, interventional tool, or other device.

Passage 1328 may be defined by one or more slits 1328a through the thickness of radiation shielding device 1300. In an example embodiment, passage 1328 may be located within a folded region 1370, such as between first and second fold locations 1371, 1372. Passage 1328 may be accessed by expanding the folded region sufficient for medical device 1360 to be positioned through passage 1328. Folded region 1370 may then be returned to a folded configuration in which passage 1328 is substantially closed around medical device 1360. A passage 1328 located within the folded region 1370 may thus prevent radiation from passing between first and second sides of radiation shielding device 1300 via passage 1328. Alternatively, or in addition, a medical device 1360 may pass between opposite sides of radiation shielding device 1300 via slits 1300c, 1300d. In various embodiments, such configurations facilitates passage of medical device 1360 through radiation shielding device 1300 while promoting a consistent and uninterrupted zone of protection for the healthcare practitioner.

Radiation shielding device 1300 may have a selected shape, including straight and/or curved edges. In some embodiments, a straight top edge may facilitate alignment with a radiation source having a complementary shape. Alternatively, or additionally, first and/or second portions 1300a, 1300b, may be expandable (e.g., by folding, rolling, etc.), such that the coverage area may be selected by a healthcare practitioner in an operating environment at the time of use.

Figure 15:
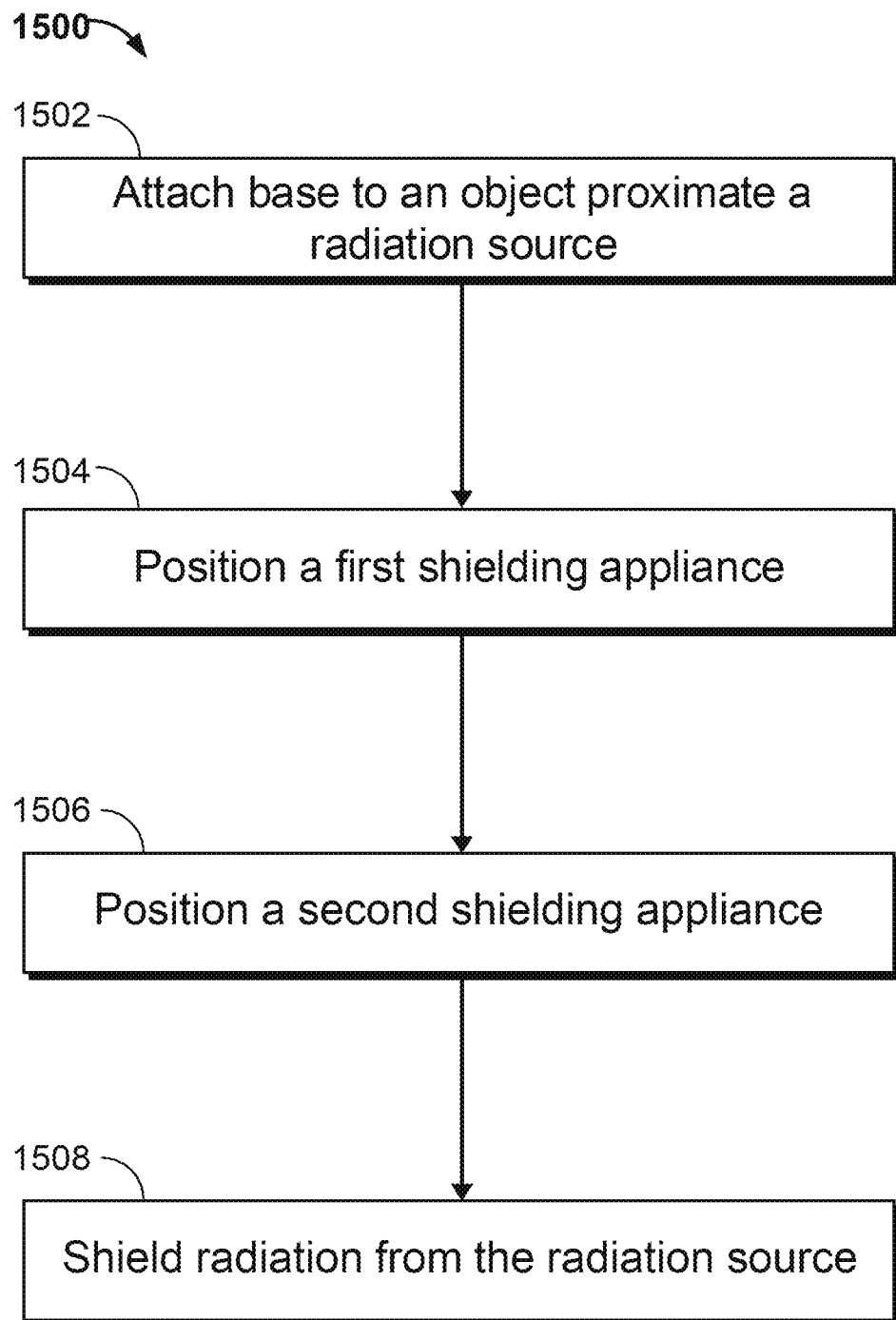
FIG. 15 is a flow diagram of an example method of shielding radiation in a medical environment.

Referring now to FIG. 15, an example flow diagram is shown illustrating a method 1500 of operating a radiation shielding device to shield a healthcare practitioner from radiation and/or liquid during a medical procedure. Method 1500 does not require a particular order of operations shown in FIG. 15 and described below, and operations may be added or eliminated.

Example method 1500 may include optional operation 1502 of attaching a base of a radiation shielding device to an object proximate a radiation source. The radiation shielding device may include one or more features of radiation shielding devices 100, 400, 900, 1100, 1300 etc. described above with reference to FIGS. 1-14. The base may be an adhesive base, and attaching the base to an object may include removing an adhesive release liner to expose an adhesive layer, and bringing the adhesive layer into contact with the object to adhere the base to the object. In various example embodiments, the object may be a patient, surgical draping on a patient, a table, bed rail, etc. The healthcare practitioner may attach the base such that the weight of radiation shielding device is supported by the object (e.g., supported by a patient). Alternatively, or additionally, attaching the base to an object may include securing the base using a hook-and-loop fastener, suction device, adjustable strap system, hook-and-loop fastener, snap-fit, sleeve positionable around a portion of a patient's body (e.g., arm or leg).

Example method 1500 may include operation 1504 of positioning a first shielding appliance (or first portion). The first shielding appliance (or first portion) may be positioned relative to a supporting object, the base, other portion of the radiation shielding device, etc. For example, a healthcare practitioner may position the first shielding appliance by rotating the first shielding appliance (e.g., about a vertical axis), tilting the first shielding appliance, or otherwise adjusting the position of first shielding appliance relative to the base (or to the second portion). In some embodiments, operation 1504 of positioning a first shielding appliance may include manipulating the shielding appliance into a desired configuration, such as folding to form first and second portions positioned at an angle relative to one another. Positioning the first shielding appliance may be performed by the healthcare practitioner in the operating room at the time of a medical operation to position the first shielding appliance to provide a selected radiation shielding zone.

In various example embodiments that include a base, positioning the first shielding appliance may occur after the first shielding device is attached to the base. For example, the first shielding device may be attached to the base when the healthcare practitioner manipulates first shielding device into a desired orientation.

In some embodiments, positioning a first shielding appliance may include attaching the first shielding appliance to the base. For example, a healthcare practitioner may attach the first shielding appliance to the base in a selected orientation (e.g., such that the first shielding appliance snaps, or is otherwise secured, into the selected orientation upon attachment to the base). Alternatively, a healthcare practitioner may first attach the first shielding appliance to the base, and subsequently manipulate the first shielding device into a selected orientation. In some example embodiments, positioning the first shielding apparatus may further include operating a locking mechanism to maintain the first shielding device in the selected orientation.

Example method 1500 may include operation 1506 of positioning a second shielding appliance (or portion) to extend away from the base. In an example embodiment, second shielding appliance (or portion) may be a relatively flexible or non-shape-stable radiation shielding drape, and/or may have one or more features as described with respect to second shielding appliance 130, 430, 930, described herein. Positioning the second shielding appliance may include draping the second shielding appliance at least partially over the object that the base is attached to, and/or may include unfolding, unrolling, etc. the second shielding appliance.

Positioning the second shielding appliance may include aligning a contoured edge of the second shielding appliance with one or more features of the base. For example, second shielding appliance may include a contoured edge configured to at least partially surround a feature of the base (e.g., a feature associated with attachment of first shielding appliance). Interference between the contoured edge of the second shielding device and the feature of the base facilitates attachment and/or positioning of the second shielding appliance relative to the base, and may prevent inadvertent positioning of the second shielding appliance over a target area where the radiation source is intended to deliver radiation to.

In various example embodiments that include a base, positioning the second shielding device may occur after the second shielding device is attached to the base. For example, the second shielding device may be attached to the base when the healthcare practitioner manipulates second shielding device into a desired orientation (e.g., by unfolding, unrolling, etc.).

In some example methods, positioning the second shielding appliance may include attaching the second shielding appliance to the base. For example, a healthcare practitioner may first attach the second shielding appliance to the base, and subsequently manipulate the second shielding device into a selected position. In some example embodiments, attaching the second shielding appliance may include adhering the second shielding appliance to an upward facing surface of the base.

In various example methods, method 1500 does not include directly attaching the first and second shielding appliances to an object that supports the radiation shielding device. In some example embodiments, method 1500 does not include directly attaching the first and second shielding appliances to any object other than the base. For example, second shielding device does not include an attachment mechanism for attaching to a patient or other object. Attachment to the base alone may promote efficient set-up and operating room workflow while facilitating a secure and stable attachment such that second radiation appliance is maintained in a selected position during a medical operation.

The healthcare practitioner may receive the radiation shielding device in a pre-assembled or partially-assembled condition in which the first shielding appliance and/or the second shielding appliance are pre-attached to the base. The first and second shielding appliances may be attached to the base before operation 1502 of attaching the base to an object, such that the first and second radiation shielding appliances are attached with the base when the base is attached to the object. Such a configuration may promote efficient set-up.

Method 1500 may include operation 1508 of shielding radiation from the radiation source by the first and second shielding appliances (or portions). A healthcare practitioner may perform a medical operation from a position opposite the radiation shielding device from a radiation source. The first and second shielding appliances provide a radiation shielding zone from which the healthcare practitioner can operate relatively freely and from a selected ergonomic configuration.

In an example method, shielding radiation occurs while the radiation shielding device is in a selected configuration, and the components of the radiation shielding device are in a relative position to one another as a result of operations 1502-1506. For example, first shielding appliance and at least a portion of second shielding appliance are positioned above the base of the radiation shielding device. The base includes attachment locations for each of the first and second radiation appliances on an upward facing side of a platform of the base (e.g., opposite aside attached to a supporting object).

While this specification contains many specific implementation details, these should not be construed as limitations on the scope of any technology or of what may be claimed, but rather as descriptions of features that may be specific to particular embodiments. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Particular embodiments of the subject matter have been described. Other embodiments are within the scope of the following claims.

What is claimed is:

1. A method of shielding scatter radiation from multiple directions in a medical environment during a medical procedure involving an imaging device, comprising:
    manipulating a radiation shielding device comprising a first shielding section and a second shielding section into a first configuration, wherein the first and second shielding sections comprise a radiation shielding material, the first and second shielding sections are integrally formed as a unitary component, and in the first configuration the first shielding section is at least partially angled relative to the second shielding section; and
    positioning the radiation shielding device relative to an imaging device such that the first shielding section extends in an orientation entirely spanning a distance between a patient and the imaging device while the imaging device is located at an operational distance from the patient.

2. The method of claim 1, wherein the radiation shielding device comprises means for securing the radiation shielding device to a surface.

3. The method of claim 2, wherein the means for securing the radiation shielding device comprises one or more adhesives located on at least one of the first and second shielding sections, and the method comprises positioning the radiation shielding device comprises removing an adhesive release liner to expose the one or more adhesives; and bringing the one or more adhesives into contact with a surface to adhere the first or second shielding sections to the surface.

4. The method of claim 1, wherein each of the first and second shielding sections include a radiation shielding material such that unsafe radiation levels on first sides of the first and second shielding sections are reduced to safe radiation levels on second sides of the first and second shielding section, and wherein the radiation shielding device is configured to protect a healthcare practitioner that may otherwise be exposed to relatively higher levels of radiation in the absence of the radiation shielding device.

5. The method of claim 4, wherein, in the first configuration, the first shielding section extends from the patient to a lower edge of the imaging device such that the radiation shielding device provides a vertical zone of radiation protection extending between the patient and imaging device.

6. The method of claim 5, comprising manipulating the first shielding section relative to the second shielding section by positioning a top edge of the first shielding section to extend to a height greater than a lower edge of the imaging device.

7. The method of claim 6, comprising manipulating the top edge of the first shielding section to impart a curve.

8. The method of claim 1, wherein the imaging device is an emitter of an imaging system.

9. The method of claim 1, wherein in the first configuration, the second shielding section is in a substantially horizontal orientation.

10. The method of claim 1, wherein the second shielding section is above the patient when the first shielding section extends in a substantially vertical orientation entirely spanning a distance between the patient and the imaging device.

11. The method of claim 1, comprising removing the radiation shielding device from a sterile package.

12. The method of claim 1, wherein the radiation shielding device comprises a malleable support member configured to maintain the first shielding section in the first configuration.

13. The method of claim 12, wherein the malleable support member comprises one or more of a malleable wire frame or a layer of malleable material.

14. The method of claim 1, wherein the radiation shielding device defines a slit located between the first shielding section and the second shielding section.

15. The method of claim 14, comprising positioning an interventional tool through the slit from a first side of the radiation shielding device to a second side of the radiation shielding device.

16. The method of claim 15, comprising articulating the first shielding section relative to the second shielding section via the slit.

17. The method of claim 1, comprising shielding radiation while the radiation shielding device is in the first configuration, wherein the first shielding section extending upwardly from the patient to a height at least equal to the imaging device, results in less radiation directed to a healthcare practitioner than with the first shielding section extending in a substantially horizontal orientation.

18. A method of shielding scatter radiation from multiple directions in a medical environment during a medical procedure involving an imaging device, comprising:
removing a radiation shielding device from a sterile package, the radiation shielding device in a first planar configuration when in the sterile package, the radiation shielding device comprising a first shielding section and a second shielding section, wherein the first and second shielding sections comprise a radiation shielding material, the first and second shielding sections are integrally formed as a unitary component;
removing an adhesive release liner from the radiation shielding device to expose an adhesive;
bringing the adhesive into contact with a surface to adhere the first or second shielding sections to the surface;
manipulating the radiation shielding device into a first configuration in which the first shielding section is at least partially angled relative to the second shielding section; and
positioning the radiation shielding device relative to an imaging device such that the first shielding section extends in an orientation entirely spanning a distance between a patient and the imaging device while the imaging device is located at an operational distance from the patient.

19. The method of claim 18, wherein the first shielding section is partially separated from the second shielding section by a slit, the slit configured to provide mobility of the first shielding section independent of the second shielding section.

20. The method of claim 19, wherein, in the first configuration, the first shielding section extends from the patient to a lower edge of the imaging device such that the radiation shielding device provides a vertical zone of radiation protection extending between the patient and imaging device, and wherein each of the first and second shielding sections include a radiation shielding material such that unsafe radiation levels on first sides of the first and second shielding sections are reduced to safe radiation levels on second sides of the first and second shielding sections.

* * * * *